(12) United States Patent
Ho et al.

(10) Patent No.: US 8,324,405 B2
(45) Date of Patent: Dec. 4, 2012

(54) CHROMENE DERIVATIVES AND USE THEREOF AS HIF HYDROXYLASE ACTIVITY INHIBITORS

(75) Inventors: Wen-bin Ho, San Francisco, CA (US); Lee Wright, San Francisco, CA (US); Shaojiang Deng, San Francisco, CA (US); Eric Turtle, San Francisco, CA (US); Lee A. Flippin, San Francisco, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 12/866,023

(22) PCT Filed: Feb. 5, 2009

(86) PCT No.: PCT/US2009/033270
§ 371 (c)(1),
(2), (4) Date: Sep. 14, 2010

(87) PCT Pub. No.: WO2009/100250
PCT Pub. Date: Aug. 13, 2009

(65) Prior Publication Data
US 2010/0331400 A1 Dec. 30, 2010

Related U.S. Application Data

(60) Provisional application No. 61/026,417, filed on Feb. 5, 2008.

(51) Int. Cl.
*C07D 311/02* (2006.01)
(52) U.S. Cl. .......................................... 549/285
(58) Field of Classification Search .............. 549/285
See application file for complete search history.

(56) References Cited

U.S. PATENT DOCUMENTS

| 4,303,664 A | 12/1981 | Ono et al. |
| 5,378,720 A | 1/1995 | Hlast et al. |
| 5,955,604 A | 9/1999 | Tsien et al. |
| 6,291,162 B1 | 9/2001 | Tsien et al. |
| 7,304,168 B2 | 12/2007 | Li et al. |
| 7,323,475 B2 | 1/2008 | Arend et al. |
| 7,618,940 B2 | 11/2009 | Fourney et al. |
| 7,629,357 B2 | 12/2009 | Arend et al. |
| 7,696,223 B2 | 4/2010 | Deng et al. |
| 7,713,986 B2 | 5/2010 | Seeley et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2005/0020487 A1 | 1/2005 | Klaus et al. |
| 2006/0148834 A1 | 7/2006 | Xu et al. |
| 2006/0178316 A1 | 8/2006 | Klaus et al. |
| 2006/0183695 A1 | 8/2006 | Klaus et al. |
| 2006/0199836 A1 | 9/2006 | Turtle et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0185159 A1 | 8/2007 | Arend et al. |
| 2007/0293575 A1 | 12/2007 | Seeley et al. |
| 2007/0298104 A1 | 12/2007 | Arend et al. |
| 2008/0004309 A1 | 1/2008 | Deng et al. |
| 2008/0293763 A1 | 11/2008 | Arend et al. |
| 2010/0047367 A1 | 2/2010 | Deng et al. |

FOREIGN PATENT DOCUMENTS

| EP | 304158 A1 | 2/1989 |
| EP | 304158 B1 | 6/1994 |
| EP | 0626378 | 11/1994 |
| WO | WO 02/074981 | 9/2002 |
| WO | WO 03/049686 | 6/2003 |
| WO | WO 03/053997 | 7/2003 |
| WO | WO 03/080566 | 10/2003 |
| WO | WO 2004/050082 | 6/2004 |
| WO | WO 2004/052284 | 6/2004 |
| WO | WO 2004/052285 | 6/2004 |
| WO | WO 2004/108121 | 12/2004 |
| WO | WO 2004/108681 | 12/2004 |
| WO | WO 2005/007192 | 1/2005 |
| WO | WO 2005/077915 | 8/2005 |
| WO | WO 2006/094292 | 9/2006 |
| WO | WO 2006/133391 | 12/2006 |
| WO | WO 2006/138511 | 12/2006 |
| WO | WO 2007/025169 | 3/2007 |
| WO | WO 2007/038571 | 4/2007 |
| WO | WO 2007/062664 A2 | 6/2007 |

(Continued)

OTHER PUBLICATIONS

Bonsignore et al. Heterocycles, 1997, 45(11), 2131-2136.*
Dorwald F. A. Side Reactions in Organic Synthesis, 2005, Wiley: VCH, Weinheim p. IX of Preface p. 1-15.*
Wolff, Burger's medicinal Chemistry and Drug Discovery, vol. 1, Principles and Practice, John Wiley & sons, New York, 1997.*
Xia et al. European Journal of Medicinal Chemistry 49 (2012) 24-40.*
Rabinowitz et al Annual Reports in Medicinal Chemistry, 2010, 45, 123-139.*
Freshney (Culture of Animal Cells, A Manual of Basic Technique, Alan R. Liss, Inc., 1983, New York, p. 4.*

(Continued)

Primary Examiner — Nizal Chandrakumar
(74) Attorney, Agent, or Firm — Foley & Lardner LLP

(57) ABSTRACT

The present invention relates to novel compounds of formula (I), methods, and compositions capable of decreasing HIF hydroxylase activity, thereby increasing the stability and/or activity of hypoxia inducible factor (HIF).

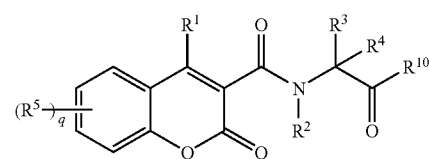

18 Claims, No Drawings

FOREIGN PATENT DOCUMENTS

| | | |
|---|---|---|
| WO | WO 2007/070359 | 6/2007 |
| WO | WO 2007/062664 A3 | 8/2007 |
| WO | WO 2007/090068 | 8/2007 |
| WO | WO 2007/103905 | 9/2007 |
| WO | WO 2007/115315 | 10/2007 |
| WO | WO 2007/136990 | 11/2007 |
| WO | WO 2007/146425 | 12/2007 |
| WO | WO 2007/146438 | 12/2007 |
| WO | WO 2007/150011 | 12/2007 |
| WO | WO 2008/076425 | 6/2008 |
| WO | WO 2008/076427 | 6/2008 |
| WO | WO 2008/089051 | 7/2008 |
| WO | WO 2008/089052 | 7/2008 |
| WO | WO 2008/130508 | 10/2008 |
| WO | WO 2008/130600 | 10/2008 |
| WO | WO 2008/137060 | 11/2008 |
| WO | WO 2008/137084 | 11/2008 |
| WO | WO 2009/039321 | 3/2009 |
| WO | WO 2009/039322 | 3/2009 |
| WO | WO 2009/039323 | 3/2009 |
| WO | WO 2009/049112 | 3/2009 |
| WO | WO 2009/070644 | 6/2009 |
| WO | WO 2009/073497 | 6/2009 |
| WO | WO 2009/073669 | 6/2009 |
| WO | WO 2009/075822 | 6/2009 |
| WO | WO 2009/075826 | 6/2009 |
| WO | WO 2009/086044 | 7/2009 |
| WO | WO 2009/089547 | 7/2009 |
| WO | WO 2010/022240 | 2/2010 |
| WO | WO 2010/056767 | 5/2010 |

OTHER PUBLICATIONS

Venkatesh et al., Role of the Development Scientist in Compound Lead Selection and Optimization J. Pharm. Sci. 89, 145-54 (2000).*

U.S. Appl. No. 12/734,895, filed Aug. 16, 2010, Arend et al.

U.S. Appl. No. 12/811,821, filed Sep. 14, 2010, Zhou et al.

Bruegge, K. et al., "Hydroxylation of Hypoxia-Inducible Transcription Factors and Chemical Compounds Targetign the HIF-alpha Hydroxylases," Current Medicinal Chemistry, vol. 14, pp. 1853-1862, XP002517838 (2007).

Wermuth, C.G., "Molecular Variants Based on Isosteric Replacements," The Practice of Medicinal Chemistry, Elsevier, pp. 189-214, XP009112544 (2003).

Leonardo Bonsignore et al., "Synthesis of 2H-1-benzopyran-2, 4 (3H)-dione-3-carboxamide and 2H, 3H-[1] benzopyrano [4, 3-b]pyrano-2-hydroxy-3-carboxamide-4, 5-dione derivatives via carbon", Heterocycles, vol. 45, No. 11, pp. 2131-2136 (1997).

* cited by examiner

CHROMENE DERIVATIVES AND USE THEREOF AS HIF HYDROXYLASE ACTIVITY INHIBITORS

CROSS-REFERENCE TO RELATED APPLICATION

This application is a National Phase application under 35 U.S.C. §371 of PCT Application PCT/US2009/033270, filed Feb. 5, 2009, which claims the benefit under 35 U.S.C. §119 (e) of U.S. Provisional Application Ser. No. 61/026,417, filed Feb. 5, 2008, which are hereby incorporated by reference in their entirety.

BACKGROUND OF THE INVENTION

1. Field of the Invention

The present invention relates to novel compounds, methods, and compositions capable of inhibiting HIF hydroxylase activity, thereby increasing the stability and/or activity of hypoxia inducible factor (HIF).

2. State of the Art

Hypoxia-inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ/ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang et al. (1996) *J. Biol. Chem.* 271:17771-17778; Iliopoulus et al. (1996) *Proc. Natl. Acad. Sci. USA,* 93:10595-10599; Maxwell et al. (1999) *Nature* 399:271-275; Sutter et al. (2000) *Proc. Natl. Acad. Sci. USA* 97:4748-4753; Cockman et al. (2000) *J. Biol. Chem.* 275:25733-25741; and Tanimoto et al. (2000) *EMBO J.* 19:4298-4309).

Levels of HIFα are elevated in most cells in response to hypoxia, and HIFα is induced in vivo when animals are subjected to ischemia or hypoxia, or develop anemia. The increase in HIFα levels leads to formation of HIFα/β complexes. HIFα/β complexes induce expression of genes whose encoded products are involved in numerous beneficial cellular processes including cytoprotective effects, increased erythropoiesis, and physiological adaptation to ischemic or hypoxic states. Induction of HIFα is potentially beneficial in conditions such as myocardial infarction, stroke, peripheral vascular disease, chronic ischemia, inflammation, and anemia.

HIFα levels can be increased by factors other than hypoxia, such as iron chelators, e.g., desferrioxamine (DFO), and divalent metal salts, e.g., $CoCl_2$. Additionally, several compounds originally identified as inhibitors of procollagen prolyl hydroxylase enzymes have been found to stabilize HIFα. Examples of such compounds can be found, e.g., in Majamaa et al. (1984) *Eur. J. Biochem.* 138:239-245; Majamaa et al. (1985) *Biochem. J.* 229:127-133; Kivirikko, and Myllyharju (1998) *Matrix Biol.* 16:357-368; Bickel et al. (1998) *Hepatology* 28:404-411; Friedman et al. (2000) *Proc. Natl. Acad. Sci. USA* 97:4736-4741; Franklin (1991) *Biochem. Soc. Trans.* 19):812-815; and Franklin et al. (2001) *Biochem. J.* 353:333-338. Additionally, compounds that stabilize HIFα have been described in, e.g., International Publication Nos. WO 03/049686, WO 02/074981, WO 03/080566, WO 2004/108681, WO 06/094292, WO 07/038,571, WO 07/090,068, and WO 07/103,905.

There remains a need for compounds that are effective in the treatment and prevention of conditions and disorders associated with HIF, including anemia, and tissue damage caused by ischemia and/or hypoxia. The compounds provided herein inhibit HIF hydroxylase activity, thereby increasing the stability and/or activity of hypoxia inducible factor (HIF), and can be used to treat and prevent HIF-associated conditions and disorders.

SUMMARY OF THE INVENTION

The present invention is directed to novel compounds and methods of using these compounds to inhibit HIF hydroxylase activity, thereby increasing the stability and/or activity of hypoxia inducible factor (HIF).

In one aspect, there are provided compounds of Formula I:

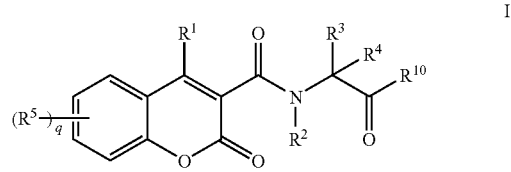

wherein:

q is 0, 1, 2, 3, or 4;

$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino;

$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl; and each $R^5$ is independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl; or two $R^5$ taken together with the carbon atoms to which they are attached form an aryl, substituted aryl, cycloalkyl, substituted cycloalkyl, heterocyclic, substituted heterocyclic, heteroaryl or substituted heteroaryl;

$R^{10}$ is —$NR^{11}R^{12}$ or —$OR^{13}$;

$R^{11}$ and $R^{12}$ are independently selected from the group consisting hydrogen, alkyl, cycloalkylene-alkylene, ($C_3$-$C_8$)heterocyclic, aryl, —C(O)($C_1$-$C_4$)alkyl, and alkyl-($C_3$-$C_8$)cycloalkylene;

or $R^{11}$ and $R^{12}$ taken together with the nitrogen to which they are attached form a 5- or 6-membered heterocyclic or substituted heterocyclic; and $R^{13}$ is selected from the group consisting of hydrogen, a cation, and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof;

provided that the compound is not [(4-hydroxy-2-oxo-2H-chromene-3-carbonyl)-amino]-acetic acid.

In one aspect, there are provided compounds of Formula II:

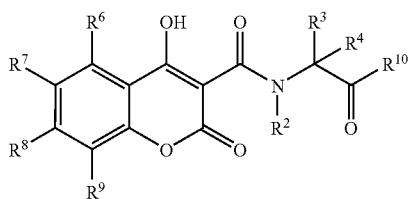

II wherein
$R^2$ is selected from the group consisting of hydrogen, alkyl, and substituted alkyl;

$R^3$ is selected from the group consisting of hydrogen, deuterium, alkyl, and substituted alkyl;

$R^4$ is selected from the group consisting of hydrogen, deuterium, and methyl; and $R^6$ and $R^9$ are independently selected from the group consisting of hydrogen, halo, alkyl, alkoxy, substituted alkoxy, cycloalkyloxy, substituted cycloalkyloxy, aryl, substituted aryl, heteroaryl, and substituted heteroaryl;

$R^7$ and $R^8$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;

or one of $R^6$ and $R^7$, $R^7$ and $R^8$, or $R^8$ and $R^9$ taken together with the carbon atoms to which they are attached optionally form an aryl, substituted aryl, cycloalkyl, substituted cycloalkyl, heterocyclic, substituted heterocyclic, heteroaryl or substituted heteroaryl;

$R^{10}$ is —$NR^{11}R^{12}$ or —$OR^{13}$;

$R^{11}$ and $R^{12}$ are independently selected from the group consisting hydrogen, alkyl, cycloalkyl-alkylene, ($C_3$-$C_8$)heterocyclic, aryl, —C(O)($C_1$-$C_4$)alkyl, and alkyl-($C_3$-$C_8$)cycloalkylene;

or $R^{11}$ and $R^{12}$ taken together with the nitrogen to which they are attached form a 5- or 6-membered heterocyclic or substituted heterocyclic; and $R^{13}$ is selected from the group consisting of hydrogen, a cation, and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof;

provided that the compound is not [(4-hydroxy-2-oxo-2H-chromene-3-carbonyl)-amino]-acetic acid.

The invention also provides pharmaceutical compositions comprising one or more compounds of Formula I or II and a pharmaceutically acceptable excipient. In some embodiments, the composition further comprises or is used in combination with at least one additional therapeutic agent. In some embodiments, the agent is selected from the group consisting of vitamin $B_{12}$, folic acid, ferrous sulfate, recombinant human erythropoietin, and an erythropoiesis stimulating agent (ESA).

The invention is also directed to methods of treating, pretreating, or delaying onset or progression of a condition associated with or mediated at least in part by hypoxia-inducible factor (HIF), the method comprising administering to a patient a therapeutically effective amount of a compound of Formula I or II, or a pharmaceutical composition comprising one or more compounds of Formula I or II. In one embodiment, the condition associated with or mediated by HIF is tissue damage associated with ischemia or hypoxia. In one aspect, the ischemia is associated with an event including, but not limited to, myocardial infarction, pulmonary embolism, intestinal infarction, ischemic stroke, renal ischemic-reperfusion injury cardiac cirrhosis, transient ischemic attack, macular degeneration, chronic kidney failure, peripheral artery disease, and congestive heart failure.

The invention is also directed to methods of treating, pretreating, or delaying onset or progression of a condition associated with or mediated, at least in part, by erythropoietin (EPO), the method comprising administering to a patient a therapeutically effective amount of a compound of Formula I or II or a pharmaceutical composition comprising one or more compounds of Formula I or II.

The invention is also directed to methods of treating, pretreating, or delaying onset of anemia, the method comprising administering to a patient a therapeutically effective amount of a compound of Formula I or II or a pharmaceutical composition comprising one or more compounds of Formula I or II.

In each of the above embodiments, the compounds of Formula I or II may or may not include [(4-hydroxy-2-oxo-2H-chromene-3-carbonyl)-amino]-acetic acid The invention is also directed to methods of inhibiting the activity of at least one HIF hydroxylase, the method comprising bringing into contact the HIF hydroxylase and a compound of the invention. In one embodiment, the HIF hydroxylase is an asparaginyl hydroxylase such as Factor Inhibiting HIF (FIH). In another embodiment, the HIF hydroxylase is a prolyl hydroxylase including, but not limited to, a HIF prolyl hydroxylase selected from the group consisting of human EGLN1, EGLN2, or EGLN3, or an orthologous enzyme from another species.

DETAILED DESCRIPTION OF THE INVENTION

Before the present compositions and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds of the Invention

The invention is directed to compounds of Formula I:

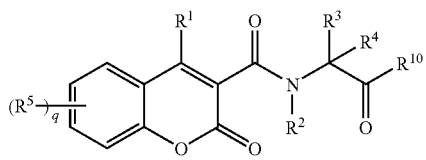

I wherein:
q is 0, 1, 2, 3, or 4;
$R^1$ is selected from the group consisting of hydroxy, acyloxy, alkoxy, substituted alkoxy, cycloalkoxy, substituted cycloalkoxy, aryloxy, substituted aryloxy, heteroaryloxy, substituted heteroaryloxy, heterocyclyloxy, substituted heterocyclyloxy, mercapto, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, amino, substituted amino, and acylamino;
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, and methyl; and
each $R^5$ is independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl; or two $R^5$ taken together with the carbon atoms to which they are attached form an aryl, substituted aryl, cycloalkyl, substituted cycloalkyl, heterocyclic, substituted heterocyclic, heteroaryl or substituted heteroaryl;
$R^{10}$ is —$NR^{11}R^{12}$ or —$OR^{13}$;
$R^{11}$ and $R^{12}$ are independently selected from the group consisting hydrogen, alkyl, cycloalkyl-alkylene, ($C_3$-$C_8$)heterocyclic, aryl, —C(O)($C_1$-$C_4$)alkyl, and alkyl-($C_3$-$C_8$)cycloalkylene;
or $R^{11}$ and $R^{12}$ taken together with the nitrogen to which they are attached form a 5- or 6-membered heterocyclic or substituted heterocyclic; and
$R^{13}$ is selected from the group consisting of hydrogen, a cation, and alkyl which is unsubstituted or substituted with one or more substituents independently selected from the group consisting of cycloalkyl, heterocyclic, aryl, and heteroaryl;

or a pharmaceutically acceptable salt, single stereoisomer, mixture of stereoisomers, ester, or prodrug thereof;
provided that the compound is not [(4-hydroxy-2-oxo-2H-chromene-3-carbonyl)-amino]-acetic acid.

In certain embodiments, the invention is directed to compounds of Formula II:

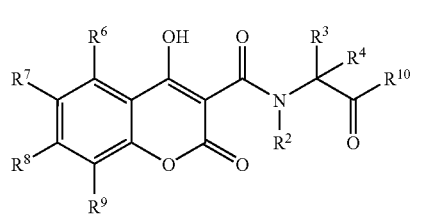

II wherein
$R^2$ is selected from the group consisting of hydrogen, alkyl, and substituted alkyl;
$R^3$ is selected from the group consisting of hydrogen, deuterium, alkyl, and substituted alkyl;
$R^4$ is selected from the group consisting of hydrogen, deuterium, and methyl; and
$R^6$ and $R^9$ are independently selected from the group consisting of hydrogen, halo, alkyl, alkoxy, substituted alkoxy, cycloalkyloxy, substituted cycloalkyloxy, aryl, substituted aryl, heteroaryl, and substituted heteroaryl;
$R^7$ and $R^8$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, hetereocyclicthio, substituted heterocyclicthio, heteroaryl, and substituted heteroaryl;
or one of $R^6$ and $R^7$, $R^7$ and $R^8$, or $R^8$ and $R^9$ taken together with the carbon atoms to which they are attached optionally form an aryl, substituted aryl, cycloalkyl, substituted cycloalkyl, heterocyclic, substituted heterocyclic, heteroaryl or substituted heteroaryl;
$R^{10}$ is —$NR^{11}R^{12}$ or —$OR^{13}$;
$R^{11}$ and $R^{12}$ are independently selected from the group consisting hydrogen, alkyl, cycloalkyl-alkylene, ($C_3$-$C_8$)heterocyclic, aryl, —C(O)($C_1$-$C_4$)alkyl, and alkyl-($C_3$-$C_8$)cycloalkylene;
or $R^{11}$ and $R^{12}$ taken together with the nitrogen to which they are attached form a 5- or 6-membered heterocyclic or substituted heterocyclic; and
$R^{13}$ is selected from the group consisting of hydrogen, a cation, and alkyl which is unsubstituted or substituted with one or more substituents independently selected from the group consisting of cycloalkyl, heterocyclic, aryl, and heteroaryl;
or a pharmaceutically acceptable salt, single stereoisomer, mixture of stereoisomers, ester, or prodrug thereof;
provided that the compound is not [(4-hydroxy-2-oxo-2H-chromene-3-carbonyl)-amino]-acetic acid.

In certain embodiments, the invention is directed to compounds of Formula I wherein q is 1 or 2.

In certain embodiments, the invention is directed to compounds of Formula I wherein $R^1$ is hydroxy.

In certain embodiments the invention is directed to compounds of Formula I wherein $R^1$ is hydroxy and $R^2$ is hydrogen. In other embodiments, the invention is directed to compounds of Formula I wherein $R^1$ is hydroxy and $R^2$ and $R^4$ are hydrogen. In other embodiments, the invention is directed to compounds of Formula II wherein $R^2$ and $R^4$ are hydrogen.

In certain embodiments, the invention is directed to compounds of Formula I or II wherein $R^2$ is hydrogen. In other embodiments, the invention is directed to compounds of Formula I or II wherein $R^3$ is hydrogen.

In certain embodiments, the invention is directed to compounds of Formula I or II wherein $R^4$ is selected from the group consisting of hydrogen and methyl.

In certain embodiments, the invention is directed to compounds of Formula I wherein each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl.

In certain embodiments, the invention is directed to compounds of Formula I wherein each $R^5$ is independently selected from the group consisting of hydrogen, halo, alkyl, substituted alkyl, aryl, substituted aryl, aryloxy, substituted aryloxy, heteroaryl, and substituted heteroaryl.

In certain embodiments, the invention is directed to compounds of Formula II wherein each of $R^6$, $R^7$, $R^8$ and $R^9$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or one of $R^6$ and $R^7$, $R^7$ and $R^8$, or $R^8$ and $R^9$ taken together with the carbon atoms to which they are attached form an aryl or substituted aryl.

In certain embodiments, the invention is directed to compounds of Formula II wherein each of $R^6$ and $R^9$ is independently selected from the group consisting of hydrogen, halo and alkyl; and each of $R^7$ and $R^8$ is independently selected from the group consisting of hydrogen, halo, alkyl substituted alkyl, aryl, substituted aryl, aryloxy, substituted aryloxy, heteroaryl, and substituted heteroaryl.

In certain embodiments, the invention is directed to compounds of Formula I or II wherein $R^{10}$ is —$OR^{13}$. In some embodiments, the invention is directed to compounds of Formula I or II wherein $R^{13}$ is hydrogen, a cation, or alkyl. In some embodiments, the invention is directed to compounds of Formula I or II wherein $R^{13}$ is $C_1$-$C_4$ alkyl.

In some embodiments, the invention is directed to compounds of Formula I
wherein
  $R^1$ is hydroxy;
  $R^2$ and $R^4$ are hydrogen;
  $R^3$ is selected from the group consisting of hydrogen, alkyl, and substituted alkyl;
  each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl; and
  $R^{10}$ is —$OR^{13}$; wherein $R^{13}$ is hydrogen, a cation or alkyl.

In some embodiments, the invention is directed to compounds of Formula I
wherein
  $R^1$ is hydroxy;
  $R^2$ and $R^4$ are hydrogen;
  $R^3$ is selected from the group consisting of hydrogen, alkyl, and substituted alkyl;
  each $R^5$ is independently selected from the group consisting of hydrogen, halo, alkyl, substituted alkyl, aryl, substituted aryl, aryloxy, substituted aryloxy, heteroaryl, and substituted heteroaryl; and
  $R^{10}$ is —$OR^{13}$; wherein $R^{13}$ is hydrogen, a cation or alkyl.

In other embodiments, the invention is directed to compounds of Formula I
wherein
  q is 1 or 2;
  $R^1$ is hydroxy;
  $R^2$ and $R^4$ are hydrogen;
  $R^3$ is selected from the group consisting of hydrogen, alkyl, and substituted alkyl;
  each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl; and
  $R^{10}$ is —$OR^{13}$; wherein $R^{13}$ is hydrogen, a cation or alkyl.

In other embodiments, the invention is directed to compounds of Formula I
wherein
  q is 1 or 2;
  $R^1$ is hydroxy;
  $R^2$ and $R^4$ are hydrogen;
  $R^3$ is selected from the group consisting of hydrogen, alkyl, and substituted alkyl;
  each $R^5$ is independently selected from the group consisting of hydrogen, halo, alkyl, substituted alkyl, aryl, substituted aryl, aryloxy, substituted aryloxy, heteroaryl, and substituted heteroaryl; and
  $R^{10}$ is —$OR^{13}$; wherein $R^{13}$ is hydrogen, a cation or alkyl.

In certain embodiments, the invention is directed to compounds of Formula I
wherein
  q is 0;
  $R^1$ is hydroxy;
  $R^2$ and $R^4$ are hydrogen;
  $R^3$ is selected from the group consisting of hydrogen, alkyl, and substituted alkyl; and
  $R^{10}$ is —$OR^{13}$; wherein $R^{13}$ is hydrogen, a cation or alkyl.

In certain embodiments, the invention is directed to compounds of Formula I wherein
  q is 1 or 2;
  $R^1$ is hydroxy;
  $R^2$ and $R^3$ are hydrogen;
  $R^4$ is selected from the group consisting of hydrogen and methyl;
  each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl; and
  $R^{10}$ is —$OR^{13}$; wherein $R^{13}$ is hydrogen, a cation or alkyl.

In certain embodiments, the invention is directed to compounds of Formula I wherein
q is 1 or 2;
$R^1$ is hydroxy;
$R^2$ and $R^3$ are hydrogen;
$R^4$ is selected from the group consisting of hydrogen and methyl;
each $R^5$ is independently selected from the group consisting of hydrogen, halo, alkyl, substituted alkyl, aryl, substituted aryl, aryloxy, substituted aryloxy, heteroaryl, and substituted heteroaryl; and
$R^{10}$ is —$OR^{13}$; wherein $R^{13}$ is hydrogen, a cation or alkyl.

In certain embodiments, the invention is directed to compounds of Formula II wherein
$R^2$ and $R^3$ are hydrogen;
$R^4$ is selected from the group consisting of hydrogen and methyl;
$R^6$ and $R^9$ are each independently selected from the group consisting of hydrogen, halo and alkyl;
$R^7$ and $R^8$ are each independently selected from the group consisting of hydrogen, halo, alkyl substituted alkyl, aryl, substituted aryl, aryloxy, substituted aryloxy, heteroaryl, and substituted heteroaryl; and
$R^{10}$ is —$OR^{13}$; wherein $R^{13}$ is hydrogen, a cation or alkyl.

Compounds of the invention include, but are not limited to, [(4-hydroxy-2-oxo-2H-chromene-3-carbonyl)-amino]-acetic acid; [(6-bromo-4-hydroxy-2-oxo-2H-chromene-3-carbonyl)-amino]-acetic acid; {[4-hydroxy-6-(4-methoxy-phenyl)-2-oxo-2H-chromene-3-carbonyl]-amino}-acetic acid; {[4-hydroxy-2-oxo-6-(4-phenoxy-phenyl)-2H-chromene-3-carbonyl]-amino}-acetic acid; {[4-hydroxy-2-oxo-6-(4-trifluoromethyl-phenyl)-2H-chromene-3-carbonyl]-amino}-acetic acid; [(4-hydroxy-6-methyl-2-oxo-2H-chromene-3-carbonyl)-amino]-acetic acid; [(8-Chloro-4-hydroxy-2-oxo-2H-chromene-3-carbonyl)-amino]-acetic acid; {[6-(4-benzyloxy-phenyl)-4-hydroxy-2-oxo-2H-chromene-3-carbonyl]-amino}-acetic acid; [(4-hydroxy-2-oxo-7-phenoxy-2H-chromene-3-carbonyl)-amino]-acetic acid; [(4-Hydroxy-7,8-dimethyl-2-oxo-2H-chromene-3-carbonyl)-amino]-acetic acid; {[4-hydroxy-2-oxo-7-(4-phenoxy-phenyl)-2H-chromene-3-carbonyl]-amino}-acetic acid; 2-(S)-{[4-hydroxy-2-oxo-7-(4-phenoxy-phenyl)-2H-chromene-3-carbonyl]-amino}-propionic acid; [(6,8-dichloro-4-hydroxy-2-oxo-2H-chromene-3-carbonyl)-amino]-acetic acid; [(6,8-dichloro-4-hydroxy-2-oxo-2H-chromene-3-carbonyl)-amino]-acetic acid ethyl ester; [(4-hydroxy-6,7-dimethyl-2-oxo-2H-chromene-3-carbonyl)-amino]-acetic acid; [(6-fluoro-4-hydroxy-2-oxo-2H-chromene-3-carbonyl)-amino]-acetic acid; [(7-fluoro-4-hydroxy-2-oxo-2H-chromene-3-carbonyl)-amino]-acetic acid; [(6,8-difluoro-4-hydroxy-2-oxo-2H-chromene-3-carbonyl)-amino]-acetic acid; [(6-chloro-4-hydroxy-8-methyl-2-oxo-2H-chromene-3-carbonyl)-amino]-acetic acid; [(4-hydroxy-8-methyl-2-oxo-2H-chromene-3-carbonyl)-amino]-acetic acid; {[6-chloro-4-hydroxy-8-(2-methyl-5-trifluoromethyl-2H-pyrazol-3-yl)-2-oxo-2H-chromene-3-carbonyl]-amino}-acetic acid; {[4-hydroxy-8-(2-methyl-5-trifluoromethyl-2H-pyrazol-3-yl)-2-oxo-2H-chromene-3-carbonyl]-amino}-acetic acid; [(6-chloro-4-hydroxy-2-oxo-8-pyridin-3-yl-2H-chromene-3-carbonyl)-amino]-acetic acid; [(6-chloro-4-hydroxy-2-oxo-8-phenyl-2H-chromene-3-carbonyl)-amino]-acetic acid; [(4-hydroxy-2-oxo-8-phenyl-2H-chromene-3-carbonyl)-amino]-acetic acid; [(6-chloro-4-hydroxy-2-oxo-8-thiophen-2-yl-2H-chromene-3-carbonyl)-amino]-acetic acid; [(4-hydroxy-2-oxo-6-thiophen-2-yl-2H-chromene-3-carbonyl)-amino]-acetic acid; [(6-furan-2-yl-4-hydroxy-2-oxo-2H-chromene-3-carbonyl)-amino]-acetic acid; [(4-hydroxy-2-oxo-6-pyridin-3-yl-2H-chromene-3-carbonyl)-amino]-acetic acid; [(4-hydroxy-2-oxo-6-pyridin-2-yl-2H-chromene-3-carbonyl)-amino]-acetic acid; [(4-hydroxy-2-oxo-2H-benzo[h]chromene-3-carbonyl)-amino]-acetic acid; [(4-hydroxy-2-oxo-2H-benzo[g]chromene-3-carbonyl)-amino]-acetic acid; [(1-hydroxy-3-oxo-3H-benzo[f]chromene-2-carbonyl)-amino]-acetic acid; [(7,10-Dibromo-4-hydroxy-2-oxo-2H-benzo[g]chromene-3-carbonyl)-amino]-acetic acid; [(4-hydroxy-7-methyl-2-oxo-2H-chromene-3-carbonyl)-amino]-acetic acid; [(7-chloro-4-hydroxy-2-oxo-2H-chromene-3-carbonyl)-amino]-acetic acid; [(4-hydroxy-6,8-diisopropyl-2-oxo-2H-chromene-3-carbonyl)-amino]-acetic acid; [(6-benzyloxy-4-hydroxy-2-oxo-2H-chromene-3-carbonyl)-amino]-acetic acid; [(6-cyclohexylmethoxy-4-hydroxy-2-oxo-2H-chromene-3-carbonyl)-amino]-acetic acid; [(6-hexyloxy-4-hydroxy-2-oxo-2H-chromene-3-carbonyl)-amino]-acetic acid; (S)-2-[(7-chloro-4-hydroxy-2-oxo-2H-chromene-3-carbonyl)-amino]-propionic acid; (S)-2-[(6-hexyloxy-4-hydroxy-2-oxo-2H-chromene-3-carbonyl)-amino]-propionic acid; (S)-2-[(6-cyclohexylmethoxy-4-hydroxy-2-oxo-2H-chromene-3-carbonyl)-amino]-propionic acid; [(4-hydroxy-6-isopropoxy-2-oxo-2H-chromene-3-carbonyl)-amino]-acetic acid; [(8-benzyloxy-4-hydroxy-2-oxo-2H-chromene-3-carbonyl)-amino]-acetic acid; [(5-benzyloxy-4-hydroxy-2-oxo-2H-chromene-3-carbonyl)-amino]-acetic acid; {[5-(4-fluoro-benzyloxy)-4-hydroxy-2-oxo-2H-chromene-3-carbonyl]-amino}-acetic acid; {[4-hydroxy-5-(4-methyl-benzyloxy)-2-oxo-2H-chromene-3-carbonyl]-amino}-acetic acid; 2-(S)-{[5-(4-fluoro-benzyloxy)-4-hydroxy-2-oxo-2H-chromene-3-carbonyl]-amino}-propionic acid; 2-(S)-{[4-hydroxy-5-(4-methyl-benzyloxy)-2-oxo-2H-chromene-3-carbonyl]-amino}-propionic acid; [(5-cyclohexyloxy-4-hydroxy-2-oxo-2H-chromene-3-carbonyl)-amino]-acetic acid; 2-(S)-[(5-cyclohexyloxy-4-hydroxy-2-oxo-2H-chromene-3-carbonyl)-amino]-propionic acid; [(7-benzyloxy-4-hydroxy-2-oxo-2H-chromene-3-carbonyl)-amino]-acetic acid; 2-(S)-[(7-benzyloxy-4-hydroxy-2-oxo-2H-chromene-3-carbonyl)-amino]-propionic acid; {[5-(3-cyclopentyl-propoxy)-4-hydroxy-2-oxo-2H-chromene-3-carbonyl]-amino}-acetic acid; 2-(S)-{[5-(3-cyclopentyl-propoxy)-4-hydroxy-2-oxo-2H-chromene-3-carbonyl]-amino}-propionic acid; [(7-cyclohexyloxy-4-hydroxy-2-oxo-2H-chromene-3-carbonyl)-amino]-acetic acid; and 2-(S)-[(7-cyclohexyloxy-4-hydroxy-2-oxo-2H-chromene-3-carbonyl)-amino]-propionic acid and pharmaceutically acceptable salts, single stereoisomers, mixture of stereoisomers, esters, and prodrugs thereof.

In some embodiments, the compounds of the invention do not include [(4-hydroxy-2-oxo-2H-chromene-3-carbonyl)-amino]-acetic acid.

2. Compositions and Methods of the Invention

The invention provides for use of a compound of Formula I or II for the manufacture of a medicament for use in treating various conditions or disorders as described herein. In one embodiment, a pharmaceutical composition or medicament is provided comprising at least one compound of Formula I or II and a pharmaceutically acceptable excipient or carrier. In certain embodiments, the methods and compositions disclosed herein comprise at least one compound of Formula I or II, provided that the compound is not [(4-hydroxy-2-oxo-2H-chromene-3-carbonyl)-amino]-acetic acid, and a pharmaceutically acceptable excipient or carrier. In certain embodiments, the methods and compositions disclosed herein comprise at least one compound of Formula I or II, including

[(4-hydroxy-2-oxo-2H-chromene-3-carbonyl)-amino]-acetic acid, and a pharmaceutically acceptable excipient or carrier.

In various embodiments, the medicament or pharmaceutical composition can further comprise or be used in combination with at least one additional therapeutic agent. In one embodiment, the agent is selected from the group consisting of vitamin $B_{12}$, ferrous sulfate, folic acid, and/or recombinant erythropoietin or an erythropoiesis stimulating agent (ESA).

The compounds of the present invention, or medicaments or compositions comprising the compounds, can be used to inhibit HIF hydroxylase activity, thereby modulating the stability and/or activity of HIF and activating HIF-regulated gene expression. The compound, or composition or medicament thereof, can be used in methods to treat, pretreat, or delay progression or onset of conditions mediated at least in part by HIF including, but not limited to, anemia and various aspects of ischemic and hypoxic conditions. Ischemic and hypoxic conditions may result from an event selected from, but not limited to, myocardial infarction, pulmonary embolism, intestinal infarction, ischemic stroke, acute respiratory failure, renal ischemic-reperfusion injury, cardiac cirrhosis, macular degeneration, neonatal respiratory distress syndrome, peripheral artery disease, chronic kidney failure, congestive heart failure, etc. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, transient ischemic attack, and systemic sclerosis. In still other embodiments, compounds may be administered to a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. In one embodiment, the compounds of the present invention, or compositions or medicaments thereof, can be used to treat, pretreat, or delay onset of anemia, such as anemia that may develop in association with various conditions or disorders. Conditions associated with anemia include, but are not limited to, acute or chronic kidney disease, diabetes, cancer, ulcers, infection with virus, e.g., HIV, bacteria, or parasites; inflammation, etc. Conditions can further include those associated with procedures or treatments including, e.g., radiation therapy, chemotherapy, dialysis, anesthesia, and surgery. Conditions associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to a method of inhibiting the activity of at least one hydroxylase enzyme which modifies the alpha subunit of hypoxia-inducible factor. The HIF hydroxylase may be an asparaginyl hydroxylase such as Factor Inhibiting HIF (FIH). The HIF hydroxylase may be a prolyl hydroxylase including, but not limited to, a prolyl hydroxylase selected from the group consisting of EGLN1, EGLN2, and EGLN3. In one embodiment, the method comprises contacting the hydroxylase with an effective amount of one or more compounds selected from the group comprising compounds of Formula I or II.

3. Definitions

It must be noted that as used herein, and in the appended claims, the singular forms "a," "an," and "the" include plural references unless the context clearly dictates otherwise.

Unless defined otherwise, all technical, and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, $18^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, $2^{nd}$ edition, Vols. I-III, Cold Spring Harbor Laboratory Press; Ausubel, F. M. et al., eds. (1999) Short Protocols in Molecular Biology, $4^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The term "HIFα" refers to the alpha subunit of hypoxia-inducible factor protein. HIFα may be any human or other mammalian protein, or fragment thereof, including, but not limited to, human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130, and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675), HIF-2α (GenBank Accession No. BAA78676), and HIF-3α (Genbank Accession No. NP_001098812). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234).

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) *J. Biol. Chem.* 272:19253-19260), amino acid 556 to 575 (Tanimoto et al., supra), amino acid 557 to 571 (Srinivas et al. (1999) *Biochem. Biophys. Res. Commun.* 260:557-561), and amino acid 556 to 575 (Ivan, and Karlin (2001) *Science* 292:464-468). Further, HIFα fragments include any fragment containing at least one occurrence of the motif LXXLAP, e.g., such as occurs in the human HIF-1α native sequence from $L_{397}$ to $P_{402}$, and from $L_{559}$ to $P_{564}$.

The terms "HIF-associated conditions" and "conditions mediated at least in part by HIF" are used inclusively and refer to any condition that can be associated with below normal, abnormal, or inappropriate modulation of HIF. HIF-associated conditions include any condition wherein an increase in HIF level would provide therapeutic benefit. HIF-associated conditions include anemic conditions and tissue damage or disorders associated with ischemic or hypoxic conditions.

The term "HIF hydroxylase" refers to any enzyme that modifies the alpha subunit of HIF by hydroxylation of one or more amino acid residues. HIF hydroxylases include Factor Inhibiting HIF (FIH) (GenBank Accession AAL27308; Mahon et al. (2001) *Genes Dev.* 15:2675-2686; Lando et al. (2002) *Science* 295:858-861; and Lando et al. (2002) *Genes Dev.* 16:1466-1471, which modifies at least one asparagine residue found within HIFα. (Also, see, Elkins et al. (2002) *J. Biol. Chem.* C200644200.) HIF hydroxylases also include HIF prolyl hydroxylases (HIF PHs), each of which modifies at least one proline residue found within HIFα.

The terms "HIF prolyl hydroxylase" and "HIF PH" refer to any enzyme that modifies the alpha subunit of HIF protein by hydroxylation of one or more proline residues. Preferably, the proline residue hydroxylated by HIF PH includes the proline found within the motif LXXLAP. HIF PH includes members of the Egl-Nine (EGLN) gene family described by Taylor (2001, *Gene* 275:125-132), and characterized by Aravind, and Koonin (2001, Genome Biol 2: RESEARCH 0007), Epstein et al. (2001, *Cell* 107:43-54), and Bruick and McKnight (2001, *Science* 294:1337-1340). HIF PH2, as used in examplary assays described herein (infra), may be any HIF PH2, e.g., human EGLN1 (GenBank Accession No. AAG33965; Dupuy et al. (2000) *Genomics* 69:348-54), mouse EGLN1 (GenBank Accession No. CAC42515), rat EGLN1 (GenBank Accession No. P59722), etc. Alternatively, another HIF PH may be used in the assay. Such HIF PH enzymes include, but are not limited to, human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AAO46039); and human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). HIF PH also includes any fragment of the foregoing full-length proteins that retains the ability to hydroxylate at least on prolyl residue in HIFα.

The term "ischemia" refers to a deficient supply of blood to a cell, tissue, organ, etc. Ischemia is associated with a reduction in nutrients, including oxygen, delivered to tissues. Ischemia may arise due to conditions such as atherosclerosis, formation of a thrombus in an artery or vein, blockage of an artery or vein by an embolus, vascular closure due to other causes, e.g., vascular spasm, etc. Such conditions may reduce blood flow, producing a state of hypoperfusion to an organ or tissue, or block blood flow completely. Other conditions that can lead to ischemia include tissue damage due to trauma or injury, such as, e.g., spinal cord injury; viral infection, which can lead to, e.g., congestive heart failure, etc. The term "ischemic condition" refers to conditions or events that are associated with or result in ischemia. Conditions associated with or resulting in ischemia include, but are not limited to, myocardial infarction, ischemic stroke, pulmonary embolism, perinatal hypoxia, circulatory shock including, e.g., hemorrhagic, septic, cardiogenic, etc., mountain sickness, acute respiratory failure, etc; intestinal infarction, acute kidney failure, renal ischemia reperfusion injury; atherosclerosis, chronic venous insufficiency, congestive heart failure, cardiac cirrhosis, diabetes, macular degeneration, sleep apnea, Raynaud's disease, systemic sclerosis, nonbacterial thrombotic endocarditis, occlusive artery disease, angina pectoris, transient ischemic attacks (TIAs), chronic alcoholic liver disease, chronic kidney failure, peripheral vascular disorders, ulcers, burns, chronic wounds etc. Ischemia can also result when individuals are placed under general anesthesia, and can cause tissue damage in organs prepared for transplant.

The terms "hypoxia" and "hypoxic" refer to an environment with levels of oxygen below normal. The term "hypoxic condition" includes, but is not limited to, ischemic conditions (ischemic hypoxia) such as those listed above, wherein hypoxia results from reduced circulation; pulmonary disorders (hypoxic hypoxia) such as COPD, severe pneumonia, pulmonary edema, pulmonary hypertension, hyaline membrane disease, and the like, wherein hypoxia results from reduced oxygenation of the blood in the lungs; anemic conditions (anemic hypoxia) such as gastric or duodenal ulcers, liver or renal disease, thrombocytopenia or blood coagulation disorders, cancer or other chronic illness, cancer chemotherapy and other therapeutic interventions that produce anemia, and the like, wherein hypoxia results from a decreased concentration of hemoglobin or red blood cells; and altitude sickness, etc.

The term "anemia" as used herein refers to any abnormality or deficiency in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or in the level of hemoglobin in blood relative to normal blood levels.

The term "anemic condition" refers to any condition, disease, or disorder associated with anemia. Anemia can arise due to various conditions, for example, acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can be associated with blood loss due to, e.g., stomach ulcers, duodenal ulcers, hemorrhoids, cancer of the stomach or large intestine, trauma, injury, surgical procedures, etc. Anemia can develop in association with radiation therapy, chemotherapy, and kidney dialysis. Anemia can also develop in HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure which results in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively herein and refer to any condition deviating from normal.

The terms "erythropoietin" and "EPO" refer to any naturally occurring, recombinant, or synthetic erythropoietin, erythropoiesis stimulating protein (ESP), or erythropoiesis stimulating agent (ESA) including, e.g., human erythropoietin (GenBank Accession No. AAA52400; Lin et al. (1985) Proc. Nat'l. Acad. Sci. USA 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), Continuous erythropoiesis receptor activator (CERA; F. Hoffmann-La Roche Ltd., Basel, Switzerland), etc.

The terms "erythropoietin-associated conditions" and "conditions mediated at least in part by erythropoietin" are used inclusively and refer to any condition that can be associated with below normal, abnormal, or inappropriate modulation of erythropoietin. EPO-associated conditions include any condition wherein an increase in EPO level would provide therapeutic benefit. Erythropoietin-associated conditions include anemic conditions such as those described above.

EPO-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The terms "treating," "treatment" and the like, are used herein to mean administering a therapy to a patient in need thereof. The therapy may be administered thereby providing a prophylactic effect in terms of completely or partially preventing a disorder or sign or symptom thereof and/or the therapy may be administered thereby providing a partial or complete cure for a disorder and/or adverse effect attributable to the disorder.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$R$^{40}$, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as trifluoromethyl, benzyl, 4-fluorobenzyl, 4-methylbenzyl, cyclohexylmethyl, 3-cyclopentylpropyl, pyrazol-1-ylmethyl, etc.

The term "alkylidene" or "alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like. "(C$_{u-v}$)alkylene" refers to alkylene groups having from u to v carbon atoms. The alkylidene or alkylene groups include branched and straight chain hydrocarbyl groups. For example "(C$_{1-6}$)alkylene" is meant to include methylene, ethylene, propylene, 2-methypropylene, pentylene, and the like.

The term "alkoxy" refers to the group "alkyl-O—" which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide," or the prefix "carbamoyl," "carboxamide," "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like. This group is exemplified by groups such as (ethanic acid-2-yl)amino, etc.

The term "acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O-substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy" or the prefix "carbamoyloxy" or "substituted carbamoyloxy," refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)N(R$^{49}$)$_2$ where each R$^{49}$ is independently selected from the group consisting of hydrogen and alkyl.

The term "aminothiocarbonylamino" refers to the group —NR$^{49}$C(S)N(R$^{49}$)$_2$ where each R$^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted hetero aryl, —NR$^{51}$S(O)$_2$—NR$^{51}$-heterocyclic, —NR$^{51}$S(O)$_2$—NR$^{51}$-substituted heterocyclic, where each R$^{51}$ is independently selected from hydrogen or alkyl, wherein each of the terms is as defined herein. This group is exemplified by groups such as 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, 4-benzyloxyphenyl, 4-methylphenyl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)β-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cation" refers to the groups, including but not limited to, Na$^+$, K$^+$, Ca$^{2+}$, Mg$^{2+}$, NH$_4^+$, N(alkyl)$_4^+$, other positively charged ions, and the like.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrrolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 2-methyl-5-trifluoromethyl-2H-pyrazol-3-yl, 1-benzyl-1H-[1,2,3]triazol-4-yl, 5-bromo-furan-2-yl etc.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO$_2$.

The term "oxo" refers to the atom (=O) or the atom (—O$^-$).

The term "sulfonyl" refers to the group —S(O)$_2$H. The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "pharmaceutically acceptable salt" refers to pharmaceutically acceptable salts of a compound, which salts are derived from a variety of organic, and inorganic counter ions well known in the art, and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the invention can be present as a mixture of stereoisomers or as a single stereoisomer.

The term "prodrug" as used herein, refers to compounds of Formula I or II that include chemical groups which, in vivo, can be converted into the carboxylate group adjacent to the —C(R$^3$)(R$^4$) substituent in compounds of Formula I and II, and/or can be split off from the amide N-atom and/or can be split off from the R$^1$ atom to provide for the active drug, a pharmaceutically acceptable salt thereof, or a biologically active metabolite thereof. Suitable groups are well known in the art and particularly include: for the carboxylic acid moiety, a prodrug selected from, e.g., esters including, but not limited to, those derived from alkyl alcohols, substituted alkyl alcohols, hydroxy substituted aryls and heteroaryls and the like; amides, particularly amides derived from amines of the formula HNR$^{200}$R$^{210}$ where R$^{200}$ and R$^{210}$ are independently hydrogen, alkyl, substituted alkyl, aryl, substituted aryl, and the like; hydroxymethyl, aldehyde and derivatives thereof.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this invention can be prepared from readily available starting materials using, for example, the following general methods, and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Synthesis of Compounds of the Invention

The compounds of this invention, A-700, are preferably prepared by, but are not limited to, the synthetic protocols illustrated in Scheme A. In Scheme A, the substituents R, $R^{20}$, $R^2$, $R^3$, $R^4$, $R^5$ $R^{10}$, $R^{11}$, $R^{12}$ and $R^{13}$ are as defined herein.

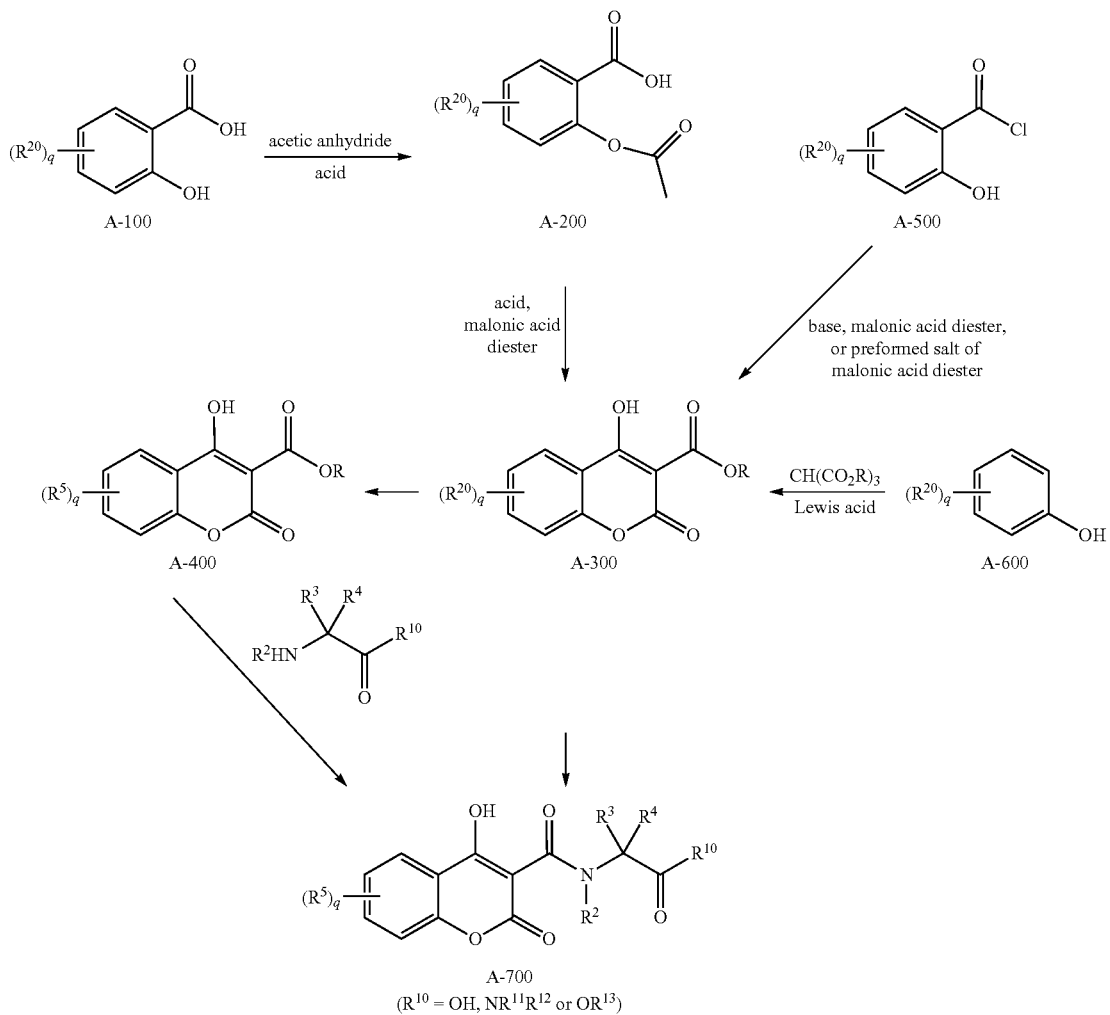

Scheme A

Compounds A-700 (when $R^{10}$=—OH) can be modified to A-700 (when $R^{10}$=—$NR^{11}R^{12}$) or A-700 (when $R^{10}$=—$OR^{13}$) under conventional amidation or esterification, respectively, which conditions are well known in the art.

Compounds A-300 and A-400 (wherein R refers to a suitable protecting group such as methyl, ethyl, etc.) are reacted with at least a stoichiometric amount and preferably an excess of a suitable alpha-amino acid (particularly, but not limited to, glycine or alanine or their corresponding salts, esters or amides). The reaction is conducted under conventional coupling conditions well known in the art. In one embodiment, the reaction is conducted in the presence of sodium methoxide, sodium ethoxide or another suitable base in methanol, DMF or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds A-700 can be recovered by conventional techniques such as neutralization, extraction, precipitation, chromatography, filtration and the like.

Compounds A-400 for use in the reactions depicted in Scheme A, can be prepared by reacting compounds A-300 ($R^{20}$ is $R^5$ or a leaving group such as, but not limited to Cl, Br, or I) with reagents $R^5M$ (M is a suitable functional group such as, but not limited to, boronic acids or their derivatives such as $C_6H_4B(OH)_2$; organozinc compounds such as benzylzinc bromide; organic magnesium compounds such as benzyl magnesium bromide; organic tin compounds such as tributylphenyltin; hydroxyl; amino; or thiol, etc.) in the presence of suitable catalyst (such as palladium catalysts including $Pd(PPh_3)_4$, $Cl_2Pd(PPh_3)_2$ or tris(dibenzylideneacetone)dipalladium(0), etc. or copper catalysts such as CuCl) and if required suitable mediators, co-catalysts and/or bases known to one skilled in the art using suitable solvents/solvent mixtures. Upon reaction completion, A-400 can be recovered by conventional techniques such as neutralization, extraction, precipitation, chromatography, filtration, and the like; or, alternatively, used in the next step without purification and/or isolation.

Compounds A-300 for use in the reactions depicted in Scheme A, can be prepared by treatment of compounds A-200 via an acid mediated alkylation/cyclization reaction using a suitable acid (preferably, but not limited to methyl sulfonic acid or concentrated sulfuric acid, at ambient or elevated temperature) with a suitable malonic acid diester (preferably, but not limited to the dimethyl or diethyl ester) using conditions well known to one skilled in the art. Alternatively, compounds A-300 can be synthesized starting with compounds A-600 via acylation and subsequent cyclization with, for example, 2-ethoxycarbonyl-malonic acid diethyl ester in the presence of a Lewis acid (preferably, but not limited to tin tetrachloride). Upon completion of either of the above reactions, the compounds A-300 can be recovered by conventional techniques such as neutralization, extraction, precipitation, chromatography, filtration and the like; or, alternatively, used in the next step without purification and/or isolation.

Alternatively, compounds A-300 for use in the reactions depicted in Scheme A, are prepared using an activated acid derivative, such as an acid chloride or mixed anhydride. Compounds A-500 are then reacted with a suitable malonic acid diester (preferably, but not limited to the dimethyl or diethyl ester) or salt thereof (preformed or generated in situ by treatment with a base, preferably, but not limited to NaH) using conditions well known to one skilled in the art (preferably, but not limited to THF at room temperature or under reflux conditions). Upon reaction completion, A-300 can be recovered by conventional techniques such as neutralization, extraction, precipitation, chromatography, filtration, and the like; or, alternatively, used in the next step without purification and/or isolation.

Compounds A-200 for use in the reactions depicted in Scheme A, can be prepared by protection of the phenolic group of compounds A-100. This is preferably done by, but not limited to, the transformation of A-100 to the corresponding acetate using conditions known to one skilled in the art (e.g., with acetic anhydride and conc. sulfuric acid at elevated temperature condition). Upon reaction completion, A-200 can be recovered by conventional techniques such as neutralization, extraction, precipitation, chromatography, filtration, and the like; or, alternatively, used in the next step without purification and/or isolation.

The compounds A-100, A-500 and A-600 for use in the reactions depicted in Scheme A are available from commercial sources.

Alternatively, compound A-300 can be prepared according to Scheme B.

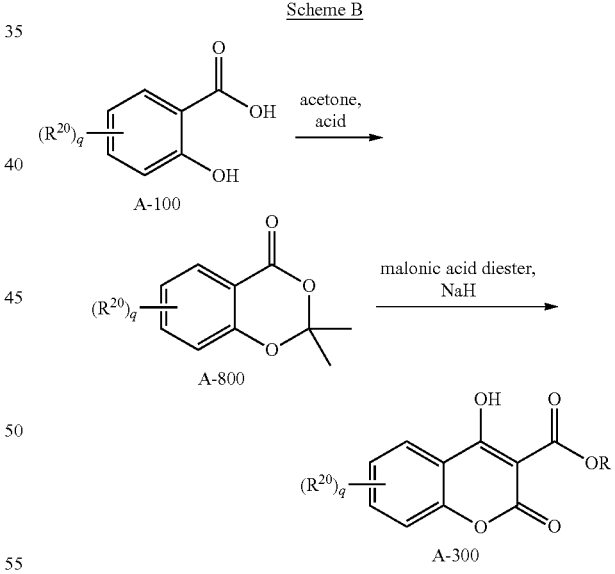

Compound A-300 can be prepared from compound A-800 by treatment of compound A-800 with a suitable malonic acid diester (preferably, but not limited to the dimethyl or diethyl ester) in the presence of a base (preferably, but not limited to sodium hydride) using conditions well known to one skilled in the art (preferably, but not limited to DMF at elevated temperature). Compound A-800 can be prepared from compound A-100 by treatment of compound A-100 with acetone or 2,2-dimethoxypropane in the presence of a suitable acid (preferably, but not limited to thionyl chloride and trifluoroacetic acid) under conditions well known to one skilled in the art (preferably, but not limited to 1,2-dimethoxyethane or trifluoroacetic anhydride at 0° C. to room temperature).

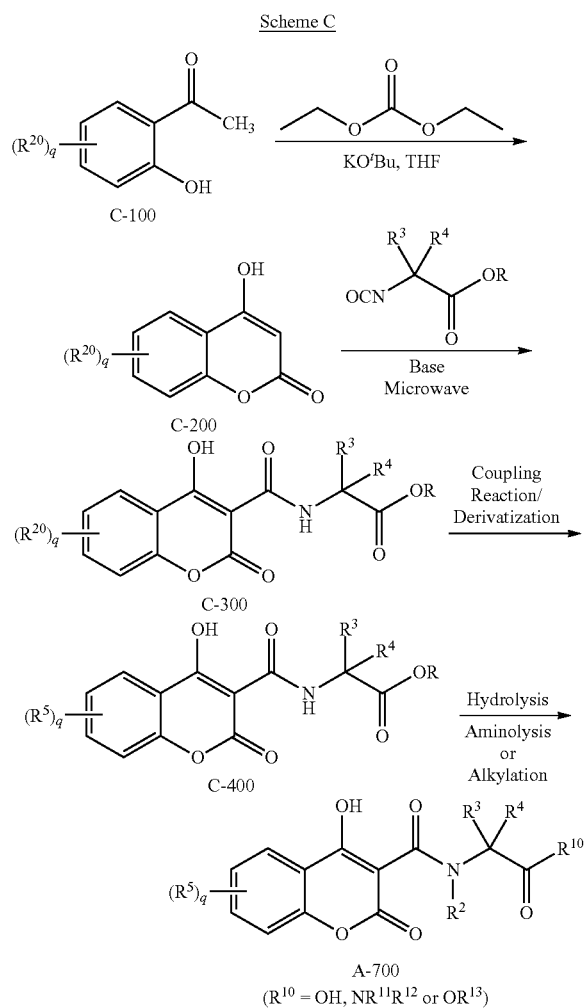

Compounds C-400 can be modified to A-700 (when $R^{10}$=—$NR^{11}R^{12}$) or A-700 (when $R^{10}$=—$OR^{13}$) under conventional aminolysis, hydrolysis, hydrogenation, or transesterification conditions well known in the art.

Compounds C-400 for use in the reactions depicted in Scheme C, can be prepared by reacting compounds C-300 ($R^{20}$ is $R^5$ or a leaving group such as, but not limited to Cl, Br, or I) with reagents $R^5M$ (M is a suitable functional group such as, but not limited to, boronic acids or their derivatives such as $C_6H_4B(OH)_2$; organozinc compounds such as benzylzinc bromide; organic magnesium compounds such as benzyl magnesium bromide; organic tin compounds such as tributylphenyltin; hydroxyl; amino; or thiol, etc.) in the presence of suitable catalyst (such as palladium catalysts including Pd(PPh$_3$)$_4$, Cl$_2$Pd(PPh3)2 or tris(dibenzylideneacetone)dipalladium(0), etc. or copper catalysts such as CuCl) and if required suitable mediators, co-catalysts and/or bases known to one skilled in the art using suitable solvents/solvent mixtures. Upon reaction completion, C-400 can be recovered by conventional techniques such as neutralization, extraction, precipitation, chromatography, filtration, and the like; or, alternatively, used in the next step without purification and/or isolation.

Compounds C-300 for use in the reactions depicted in Scheme C, can be prepared by reacting compounds C-200 ($R^{20}$ is $R^5$ or a leaving group such as, but not limited to Cl, Br, or I) with reagents including, but not limited to, isocyanates, isothiocyanates, and acyl halides in the presence of suitable base such as triethylamine and, if required, facilitated by microwave irradiation, sonication or appropriate methods known to one skilled in the art using suitable solvents/solvent mixtures. Upon reaction completion, C-300 can be recovered by conventional techniques such as neutralization, extraction, precipitation, chromatography, filtration, and the like; or, alternatively, used in the next step without purification and/or isolation.

Compounds C-200 for use in the reactions depicted in Scheme C, can be prepared by treatment of compounds C-100 with dialkyl carbonates in the presence of strong bases such as potassium tert-butoxide in suitable solvents using conditions well known to one skilled in the art. Upon completion of either of the above reactions, the compounds C-200 can be recovered by conventional techniques such as neutralization, extraction, precipitation, chromatography, filtration and the like; or, alternatively, used in the next step without purification and/or isolation.

The compounds C-100 for use in the reactions depicted in Scheme C are available from commercial sources.

Other modifications to arrive at compounds of this invention are well within the skill of the art. For example, modification of the C-4 hydroxy group may be done by conventional means to corresponding alkoxy, acyloxy etc. groups to provide compounds of formula I.

5. Use of Compounds of the Invention

The compounds of the present invention can be used to inhibit HIF hydroxylase activity, thereby modulating the stability and/or activity of HIF and activating HIF-regulated gene expression. The compounds can be used in methods to treat, pretreat, or delay progression or onset of conditions associated with HIF including, but not limited to, anemia and various aspects of ischemic and hypoxic conditions. In various embodiments, the compound is administered immediately following a condition associated with ischemia, e.g., myocardial infarction, pulmonary embolism, intestinal infarction, ischemic stroke, renal ischemic-reperfusion injury, cardiac cirrhosis, macular degeneration, pulmonary embolism, acute respiratory failure, neonatal respiratory distress syndrome, and congestive heart failure. In another embodiment, the compound is administered immediately after a trauma or injury. In other embodiments, the compound can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

In particular embodiments, the compounds of the present invention can be used to increase endogenous erythropoietin (EPO). The compounds can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

6. Testing and Administration

The biological activity of the compounds of the invention may be assessed using any conventionally known methods. Suitable assay methods are well known in the art. The following assays are presented only as examples and are not intended to be limiting. The compounds of the invention are active in at least one of the following assays.

i. Cell-Based HIFα Stabilization Assay

Human cells derived from various tissues are separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media is replaced with OPTI-MEM media (Invitrogen Life Technologies, Carlsbad Calif.), and cell layers are incubated for approximately 24 hours in 20% $O_2$, 5% $CO_2$ at 37° C. Compound or 0.013% DMSO (dimethyl sulfoxide) is then added to existing medium and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 μL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

ii. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

iii. HIF-PH Assay

Ketoglutaric acid α-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. For example, a HIF peptide for use in the HIF-PH assay is [methoxycoumarin]-DLDLEALAPYIPAD-DDFQL-amide. HIF-PH, e.g., HIF-PH2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, Methods Enzymol. 82:245-304). Assay reactions contain 50 mM HEPES (pH 7.4), 100 μM α-ketoglutaric acid sodium salt, 0.30 μCi/mL ketoglutaric acid α-[1-$^{14}$C]-sodium salt, 40 μM $FeSO_4$, 1 mM ascorbate, 1541.8 units/mL Catalase, with or without 50 μM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

Representative compounds of the invention were analyzed using the HIF-PH assay described above. Table I presents enzyme inhibition data for exemplary compounds against HIF-PH2, a representative HIF prolyl hydroxylase. By inhibiting HIF prolyl hydroxylase, compounds of the invention stabilize HIFα, which then combines with HIFβ to form an active transcription factor that increases expression of various genes involved in numerous beneficial cellular processes.

TABLE 1

| No. | Name | Concentration (μM) | % Inhibition HIF-PH2 |
|---|---|---|---|
| 1 | [(4-Hydroxy-2-oxo-2H-chromene-3-carbonyl)-amino]-acetic acid | 22.22 | 96 |
| 2 | [(6-Bromo-4-hydroxy-2-oxo-2H-chromene-3-carbonyl)-amino]-acetic acid | 22.22 | 97 |
| 3 | {[4-Hydroxy-6-(4-methoxy-phenyl)-2-oxo-2H-chromene-3-carbonyl]-amino}-acetic acid | 7.41 | 94 |
| 4 | {[4-Hydroxy-2-oxo-6-(4-phenoxy-phenyl)-2H-chromene-3-carbonyl]-amino}-acetic acid | 7.41 | 100 |
| 5 | {[4-Hydroxy-2-oxo-6-(4-trifluoromethyl-phenyl)-2H-chromene-3-carbonyl]-amino}-acetic acid | 7.41 | 96 |
| 6 | [(4-Hydroxy-6-methyl-2-oxo-2H-chromene-3-carbonyl)-amino]-acetic acid | 200.00 | 100 |
| 7 | [(8-Chloro-4-hydroxy-2-oxo-2H-chromene-3-carbonyl)-amino]-acetic acid | 200.00 | 100 |
| 8 | {[6-(4-Benzyloxy-phenyl)-4-hydroxy-2-oxo-2H-chromene-3-carbonyl]-amino}-acetic acid | 22.22 | 100 |
| 9 | [(4-Hydroxy-2-oxo-7-phenoxy-2H-chromene-3-carbonyl)-amino]-acetic acid | 22.22 | 100 |
| 10 | [(4-Hydroxy-7,8-dimethyl-2-oxo-2H-chromene-3-carbonyl)-amino]-acetic acid | 22.22 | 100 |
| 11 | {[4-Hydroxy-2-oxo-7-(4-phenoxy-phenyl)-2H-chromene-3-carbonyl]-amino}-acetic acid | 22.22 | 100 |
| 12 | 2-S-{[4-Hydroxy-2-oxo-7-(4-phenoxy-phenyl)-2H-chromene-3-carbonyl]-amino}-propionic acid | 22.22 | 100 |
| 13 | [(6,8-Dichloro-4-hydroxy-2-oxo-2H-chromene-3-carbonyl)-amino]-acetic acid | 22.22 | 96 |
| 14 | [(6,8-Dichloro-4-hydroxy-2-oxo-2H-chromene-3-carbonyl)-amino]-acetic acid ethyl | 200.00 | 43 |
| 15 | [(4-Hydroxy-6,7-dimethyl-2-oxo-2H-chromene-3-carbonyl)-amino]-acetic acid | 12.50 | 98 |

TABLE 1-continued

| No. | Name | Concentration (µM) | % Inhibition HIF-PH2 |
|-----|------|--------------------|-----------------------|
| 16 | [(6-Fluoro-4-hydroxy-2-oxo-2H-chromene-3-carbonyl)-amino]-acetic acid | 12.50 | 96 |
| 17 | [(7-Fluoro-4-hydroxy-2-oxo-2H-chromene-3-carbonyl)-amino]-acetic acid | 12.50 | 98 |
| 18 | [(6,8-Difluoro-4-hydroxy-2-oxo-2H-chromene-3-carbonyl)-amino]-acetic acid | 12.50 | 95 |
| 19 | [(6-Chloro-4-hydroxy-8-methyl-2-oxo-2H-chromene-3-carbonyl)-amino]-acetic acid | 50.00 | 99 |
| 20 | [(4-Hydroxy-8-methyl-2-oxo-2H-chromene-3-carbonyl)-amino]-acetic acid | 50.00 | 99 |
| 21 | {[6-Chloro-4-hydroxy-8-(2-methyl-5-trifluoromethyl-2H-pyrazol-3-yl)-2-oxo-2H-chromene-3-carbonyl]-amino}-acetic acid | 50.00 | 99 |
| 23 | [(6-Chloro-4-hydroxy-2-oxo-8-pyridin-3-yl-2H-chromene-3-carbonyl)-amino]-acetic acid | 50.00 | 99 |
| 27 | [(4-Hydroxy-2-oxo-6-thiophen-2-yl-2H-chromene-3-carbonyl)-amino]-acetic acid | 12.50 | 99 |
| 28 | [(6-Furan-2-yl-4-hydroxy-2-oxo-2H-chromene-3-carbonyl)-amino]-acetic acid | 12.50 | 100 |
| 29 | [(4-Hydroxy-2-oxo-6-pyridin-3-yl-2H-chromene-3-carbonyl)-amino]-acetic acid | 50.00 | 97 |
| 30 | [(4-Hydroxy-2-oxo-6-pyridin-2-yl-2H-chromene-3-carbonyl)-amino]-acetic acid | 50.00 | 99 |
| 31 | [(4-Hydroxy-2-oxo-2H-benzo[h]chromene-3-carbonyl)-amino]-acetic acid | 12.50 | 100 |
| 32 | [(4-Hydroxy-2-oxo-2H-benzo[g]chromene-3-carbonyl)-amino]-acetic acid | 12.50 | 98 |
| 33 | [(1-Hydroxy-3-oxo-3H-benzo[f]chromene-2-carbonyl)-amino]-acetic acid | 200.00 | 100 |
| 34 | [(7,10-Dibromo-4-hydroxy-2-oxo-2H-benzo[g]chromene-3-carbonyl)-amino]-acetic acid | 12.50 | 100 |
| 35 | [(4-Hydroxy-7-methyl-2-oxo-2H-chromene-3-carbonyl)-amino]-acetic acid | 12.50 | 97 |
| 46 | [(5-Benzyloxy-4-hydroxy-2-oxo-2H-chromene-3-carbonyl)-amino]-acetic acid | 50.00 | 99 |
| 47 | {[5-(4-Fluoro-benzyloxy)-4-hydroxy-2-oxo-2H-chromene-3-carbonyl]-amino}-acetic acid | 50.00 | 99 |
| 48 | {[4-Hydroxy-5-(4-methyl-benzyloxy)-2-oxo-2H-chromene-3-carbonyl]-amino}-acetic acid | 50.00 | 99 |

7. Pharmaceutical Formulations and Routes of Administration

The compositions of the present invention can be delivered directly or in pharmaceutical compositions or medicaments along with suitable carriers or excipients, as is well known in the art. Present methods of treatment can comprise administration of an effective amount of a compound of the invention to a subject in need; e.g., a subject having or at risk for anemia due to, e.g., chronic renal failure, diabetes, cancer, AIDS, radiation therapy, chemotherapy, kidney dialysis, or surgery; or, e.g., a subject having or at risk for ischemia due to, e.g., myocardial infarction, congestive heart failure, cardiac cirrhosis, pulmonary insufficiency, atherosclerosis, peripheral vascular disease, or the like. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius (° C.). Also, in these examples and elsewhere, abbreviations have the following meanings:

| | |
|---|---|
| μL = | Microliter |
| μM = | Micromolar |
| aq = | aqueous |
| br s = | Broad singlet |
| d = | Doublet |
| DCC = | Dicyclohexylcarbodiimide |
| DCCU = | Dicyclohexyl urea |
| dd = | Double doublet |
| DMAP = | 4-Dimethylaminopyridine |
| DME = | 1,2-dimethoxyethane |
| DMF = | Dimethyl formamide |
| DMSO = | Dimethyl sulfoxide |
| EDTA = | Ethylenediamine tetraacetic acid |
| ESI MS and MS ESI = | Electrospray Ionization Mass Spectrometry |
| EtOH = | Ethanol |
| EtOAc = | Ethyl acetate |
| g = | Gram |
| h = | Hour |
| HOBT = | 1-Hydroxybenzotriazole |
| Hz = | Hertz |
| L = | Liter |
| M = | Molar |
| m = | Multiplet |
| m/z and m/e = | Mass to charge ratio |
| MeOH = | Methanol |

-continued

| | |
|---|---|
| mg = | Milligram |
| $MgSO_4$ = | Magnesium sulfate |
| MHz = | Mega Hertz |
| min = | Minute |
| mL = | Milliliter |
| mM = | Millimolar |
| mmol = | Millimole |
| mol = | Mole |
| MS = | Mass spectroscopy |
| N = | Normal |
| NaOMe = | Sodium methoxide |
| NMR = | Nuclear magnetic resonance |
| $PPh_3$ = | Triphenyl phosphine |
| ppm = | Parts per million |
| $Pd(PPh_3)_2Cl_2$ = | Dichlorobis(triphenylphosphine)palladium(II) |
| $Pd(PPh_3)_4$ = | tetrakis(triphenylphosphine)palladium(0) |
| q = | Quartet |
| rt = | Room temperature |
| s = | Singlet |
| SGC = | Silica gel chromatography |
| t = | Triplet |
| THF = | Tetrahydrofuran |

Example 1

[(4-Hydroxy-2-oxo-2H-chromene-3-carbonyl)-amino]-acetic acid a) 4-Hydroxy-2-oxo-2H-chromene-3-carboxylic acid methyl ester To a mixture of O-acetylsalicyloyl chloride (Alfa Aesar, 1.0 g, 5.05 mmol) in THF (10 mL) at 0° C. was added sodium hydride (60% dispersed in mineral oil, 263 mg, 6.57 mmol). It was stirred at 0° C. for 15 min prior to the addition of a solution of dimethyl malonate (0.67 g, 5.05 mmol) in THF (5 mL) at 0° C. The resulting mixture was stirred at 0° C. for 5 min and then at rt for 2.5 h, and was concentrated. The residue was taken up in water (50 mL), acidified by 1 N HCl aqueous solution, and extracted with EtOAc (2×100 mL). Combined organic layers were washed with brine, dried over $MgSO_4$, filtered and concentrated to give the intermediate (2-(2-acetoxy-benzoyl)-malonic acid dimethyl ester) (1.45 g) as an oil. The intermediate (1.26 g, 4.28 mmoL) was treated with (1/1) MeOH/10% aq HCl (26 mL) and heated to 75° C. (oil bath temperature) for 30 min and then at rt overnight. White precipitate formed during the reaction was collected, rinsed with water and dried in vacuo to give the title compound (555 mg). MS ESI(+) m/e: 221 (M+1).

b) [(4-Hydroxy-2-oxo-2H-chromene-3-carbonyl)-amino]-acetic acid

To a mixture of 4-hydroxy-2-oxo-2H-chromene-3-carboxylic acid methyl ester (150 mg, 0.68 mmol) in DMF (12 mL) was added glycine (1.03 g, 13.6 mmol) and NaOMe (0.5 M in MeOH, 20.4 mL, 10.2 mmol) at rt. It was concentrated in an evaporator to remove most MeOH solvent. The resulting mixture was refluxed for 2 h. After cooled, it was diluted with water (100 mL) and acidified by 1 N HCl to pH=3-4. Precipitate was collected, rinsed with water and dried in vacuo. Crude solid was triturated in hexanes, and solid product was collected and dried to give the title compound (76 mg). MS ESI(+) m/e: 264 (M+1).

Example 2

[(6-Bromo-4-hydroxy-2-oxo-2H-chromene-3-carbonyl)-amino]-acetic acid a) 2-Acetoxy-5-bromo-benzoic acid

To a mixture of 2-hydroxy-5-bromo-benzoic acid (5.0 g, 23.0 mmol) in acetic anhydride (7.1 mL, 75.4 mmol) was added conc. $H_2SO_4$ (0.35 mL) at rt. Resulting suspension was heated in a 100° C. oil bath for 25 min. After cooled to about 50° C., the reaction mixture was poured onto ice (100 g) with stirring. The precipitated product was collected, rinsed with water, and dried in vacuo to give the title compound (5.56 g). $^1$H NMR (200 MHz, $CDCl_3$): δ (ppm)=8.21 (d, J=2.3 Hz, 1H), 7.71 (dd, J=8.6, 2.3 Hz, 1H), 7.01 (d, J=8.6 Hz, 1H), 2.34 (s, 3H).

b) 6-Bromo-4-hydroxy-2-oxo-2H-chromene-3-carboxylic acid methyl ester

To a mixture of 2-acetoxy-5-bromo-benzoic acid (2.0 g, 7.72 mmol) in anhydrous THF (30 mL) at 0° C. was added HOBT (1.04 g, 7.72 mmol) and then DCC (1.59 g, 7.72 mmol). Resulting mixture was stirred at 0° C. for 1 h and the suspension was refrigerated overnight at 3-5° C. The precipitated solid (DCCU) was filtered off to give Solution 1. In another flask, dimethylmalonate (1.02 g, 7.72 mmol) was dissolved in anhydrous THF (15 mL) and cooled to 0° C., and to the mixture was added NaH solid (60% dispersed in mineral oil) (401 mg, 10.04 mmol). The suspension was stirred at 0° C. for 15 min prior to the addition of Solution 1. The resulting mixture was stirred at 0° C. for 5 min and at rt for 2.5 h and then concentrated in vacuo. The residue was diluted with water (100 mL), acidified to pH=3-4 using 4 N aq HCl, and extracted with EtOAc. Organic layer was washed with brine, dried over $MgSO_4$, filtered, and concentrated. The residue was treated with (1/1) MeOH/10% HCl aqueous solution (60 mL) and refluxed for 2 h. After cooled, reaction mixture was diluted with water (50 mL). White precipitate was collected, rinsed with water and dried in vacuo. The product was triturated with hexanes and dried to give the title compound (1.46 g). MS ESI(−) m/e: 297, 299 (M−1).

c) [(6-Bromo-4-hydroxy-2-oxo-2H-chromene-3-carbonyl)-amino]-acetic acid

[(6-Bromo-4-hydroxy-2-oxo-2H-chromene-3-carbonyl)-amino]-acetic acid was prepared under conditions analogous to example 1-b. MS ESI(−) m/e: 340, 342 (M−1).

Example 3

{[4-Hydroxy-6-(4-methoxy-phenyl)-2-oxo-2H-chromene-3-carbonyl]-amino}-acetic acid a) 4-Hydroxy-6-(4-methoxy-phenyl)-2-oxo-2H-chromene-3-carboxylic acid methyl ester To a mixture of 6-bromo-4-hydroxy-2-oxo-2H-chromene-3-carboxylic acid methyl ester (150 mg, 0.5 mmol; example 2-b) in dimethoxyethane (DME) was added 4-methoxyphenylboroic acid (92 mg, 0.6 mmol), tetrakis(triphenylphosphine)palladium(0) (58 mg, 0.05 mmol) and 2N aq $Na_2CO_3$ (0.62 mL). The resulting mixture was purged with $N_2$ for 1 min and heated to reflux for 2 h. Reaction mixture was diluted with water (50 mL) and acidified by 1 N aq HCl to pH=3-4. Precipitate was collected and dissolved in EtOAc. Insoluble was filtered off and the filtrate was dried over $MgSO_4$, filtered, and concentrated. The crude product was triturated with MeOH (10 mL) and filtered. Resulting solid was dried in vacuo to give the title compound (112 mg). MS ESI(+) m/e: 327 (M+1).

b) {[4-Hydroxy-6-(4-methoxy-phenyl)-2-oxo-2H-chromene-3-carbonyl]-amino}-acetic acid {[4-Hydroxy-6-(4-methoxy-phenyl)-2-oxo-2H-chromene-3-carbonyl]-amino}-acetic acid was prepared from 4-hydroxy-6-(4-methoxy-phenyl)-2-oxo-2H-chromene-3-carboxylic acid methyl ester under conditions analogous to example 1-b. MS ESI(−) m/e: 368 (M−1).

Example 4

{[4-Hydroxy-2-oxo-6-(4-phenoxy-phenyl)-2H-chromene-3-carbonyl]-amino}-acetic acid a) 4-Hydroxy-2-oxo-6-(4-phenoxy-phenyl)-2H-chromene-3-carboxylic acid methyl ester 4-Hydroxy-2-oxo-6-(4-phenoxy-phenyl)-2H-chromene-3-carboxylic acid methyl ester was prepared from 6-bromo-4-hydroxy-2-oxo-2H-chromene-3-carboxylic acid methyl ester and 4-phenoxyphenylboronic acid under conditions analogous to example 3-a. MS ESI(+) m/e: 389 (M+1).

b) {[4-Hydroxy-2-oxo-6-(4-phenoxy-phenyl)-2H-chromene-3-carbonyl]-amino}-acetic acid {[4-Hydroxy-2-oxo-6-(4-phenoxy-phenyl)-2H-chromene-3-carbonyl]-amino}-acetic acid was prepared from 4-hydroxy-2-oxo-6-(4-phenoxy-phenyl)-2H-chromene-3-carboxylic acid methyl ester under conditions analogous to example 1-b. MS ESI(−) m/e: 430 (M−1).

Example 5

{[4-Hydroxy-2-oxo-6-(4-trifluoromethyl-phenyl)-2H-chromene-3-carbonyl]-amino}-acetic acid a) 4-Hydroxy-2-oxo-6-(4-trifluoromethyl-phenyl)-2H-chromene-3-carboxylic acid methyl ester 4-Hydroxy-2-oxo-6-(4-trifluoromethyl-phenyl)-2H-chromene-3-carboxylic acid methyl ester was prepared from 6-bromo-4-hydroxy-2-oxo-2H-chromene-3-carboxylic acid methyl ester and 4-(trifluoromethyl)phenylboronic acid under conditions analogous to example 3-a. MS ESI(+) m/e: 365 (M+1).

b) {[4-Hydroxy-2-oxo-6-(4-trifluoromethyl-phenyl)-2H-chromene-3-carbonyl]-amino}-acetic acid {[4-Hydroxy-2-oxo-6-(4-trifluoromethyl-phenyl)-2H-chromene-3-carbonyl]-amino}-acetic acid was prepared from 4-hydroxy-2-oxo-6-(4-trifluoromethyl-phenyl)-2H- chromene-3-carboxylic acid methyl ester under conditions analogous to example 1-b. MS ESI(−) m/e: 406 (M−1).

Example 6

[(4-Hydroxy-6-methyl-2-oxo-2H-chromene-3-carbonyl)-amino]-acetic acid a) 4-Hydroxy-6-methyl-2-oxo-2H-chromene-3-carboxylic acid methyl ester 4-Hydroxy-6-methyl-2-oxo-2H-chromene-3-carboxylic acid methyl ester was prepared from 6-bromo-4-hydroxy-2-oxo-2H-chromene-3-carboxylic acid methyl ester under conditions analogous to example 3-a. The obtained product was purified by silica gel chromatography (eluting with 2%-10% MeOH in methylene chloride) to give the title compound. MS ESI(+) m/e: 235 (M+1).

b) [(4-Hydroxy-6-methyl-2-oxo-2H-chromene-3-carbonyl)-amino]-acetic acid

[(4-Hydroxy-6-methyl-2-oxo-2H-chromene-3-carbonyl)-amino]-acetic acid was prepared from 4-hydroxy-6-methyl-2-oxo-2H-chromene-3-carboxylic acid methyl ester under conditions analogous to example 1-b. MS ESI(−) m/e: 276 (M−1).

Example 7

[(8-Chloro-4-hydroxy-2-oxo-2H-chromene-3-carbonyl)-amino]-acetic acid a) 2-Acetoxy-3-chloro-benzoic acid To a mixture of 2-hydroxy-3-chloro-benzoic acid (5.0 g, 29.0 mmol) in acetic anhydride (9.0 mL, 95.6 mmol) was added conc. $H_2SO_4$ (0.44 mL) at rt. Resulting suspension was heated in a 100° C. oil bath for 40 min. After cooled to about 50° C., the reaction mixture was poured onto ice (100 g) with stirring. Liquid was decanted off and the gooey residue was dissolved in methylene chloride, washed with water and brine, and dried over $MgSO_4$. It was then filtered, and concentrated to give the title compound (5.89 g). $^1$H NMR (200 MHz, $CDCl_3$): δ (ppm)=7.99 (dd, J=7.8, 1.6 Hz, 1H), 7.66 (dd, J=7.8, 1.6 Hz, 1H), 7.28 (m, 1H), 2.39 (s, 3H).

b) 8-Chloro-4-hydroxy-2-oxo-2H-chromene-3-carboxylic acid methyl ester

8-Chloro-4-hydroxy-2-oxo-2H-chromene-3-carboxylic acid methyl ester was prepared under conditions analogous to example 2-b. The crude product obtained was triturated in methylene chloride and filtered. The solid was then recrystallized from hot MeOH/methylene chloride to give the title compound. $^1$H NMR (200 MHz, $CDCl_3$): δ (ppm)=7.93 (dd, J=7.8, 1.6 Hz, 1H), 7.73 (dd, J=7.8, 1.6 Hz, 1H), 7.26 (m, 1H), 4.04 (s, 3H).

c) [(8-Chloro-4-hydroxy-2-oxo-2H-chromene-3-carbonyl)-amino]-acetic acid

A mixture of 8-chloro-4-hydroxy-2-oxo-2H-chromene-3-carboxylic acid methyl ester (150 mg, 0.59 mmol) and glycine sodium salt (286 mg, 2.95 mmol) in 2-methoxyethanol (6 mL) was heated to reflux overnight. Reaction mixture was concentrated and dissolved in water (25 mL). The solution was acidified by 1 N aq HCl to pH=2-3 and extracted with EtOAc. Organic layer was washed with water, brine, dried over MgSO4, filtered and concentrated to give the title compound (135 mg). MS ESI(−) m/e: 296 (M−1).

Example 8

{[6-(4-Benzyloxy-phenyl)-4-hydroxy-2-oxo-2H-chromene-3-carbonyl]-amino}-acetic acid a) 6-(4-Benzyloxy-phenyl)-4-hydroxy-2-oxo-2H-chromene-3-carboxylic acid methyl ester 6-(4-Benzyloxy-phenyl)-4-hydroxy-2-oxo-2H-chromene-3-carboxylic acid methyl ester was prepared from 6-bromo-4-hydroxy-2-oxo-2H-chromene-3-carboxylic acid methyl ester (example 2-b) and 4-benzyloxyphenylboronic acid under conditions analogous to example 3-a. $^1$H NMR (200 MHz, $CDCl_3$): δ (ppm)=8.14 (d, J=2.3 Hz, 1H), 7.85 (dd, J=8.5, 2.3 Hz, 1H), 7.54-7.08 (m, 10H), 5.12 (s, 2H), 4.04 (s, 3H).

b) {[6-(4-Benzyloxy-phenyl)-4-hydroxy-2-oxo-2H-chromene-3-carbonyl]-amino}-acetic acid {[6-(4-Benzyloxy-phenyl)-4-hydroxy-2-oxo-2H-chromene-3-carbonyl]-amino}-acetic acid was prepared under conditions analogous to example 7-c. MS ESI(−) m/e: 444 (M−1).

Example 9

[(4-Hydroxy-2-oxo-7-phenoxy-2H-chromene-3-carbonyl)-amino]-acetic acid a) 4-Hydroxy-2-oxo-7-phenoxy-2H-chromene-3-carboxylic acid ethyl ester A mixture of 3-phenoxy-phenol (1.068 g, 5.73 mmol), 2-ethoxycarbonyl-malonic acid diethyl ester (3.65 mL, 17.2 mmol), and tin tetrachloride (14 μL, 0.11 mmol) was heated in a 200° C.-oil bath for 5 min; then cooled, the reaction mixture was directly purified on silica gel column chromatography (eluent: ethyl acetate in dichloromethane: 10% to 80%) to give the desired title product (84 mg, 4.4%). ESI (m/z): 327 (M+H)$^+$.

b) [(4-Hydroxy-2-oxo-7-phenoxy-2H-chromene-3-carbonyl)-amino]-acetic acid

A mixture of 4-hydroxy-2-oxo-7-phenoxy-2H-chromene-3-carboxylic acid ethyl ester (84 mg, 0.248 mmol) and sodium glycinate (121 mg, 1.24 mmol) in methoxyethanol (5 mL) was refluxed for 15 h; then cooled, the solvent was removed, the residue was redissolved in water, acidified with 2 M HCl, the precipitates were collected and freeze dried to give the desired title product (93 mg). ESI (m/z): 356 (M+H)$^+$.

Example 10

[(4-Hydroxy-7,8-dimethyl-2-oxo-2H-chromene-3-carbonyl)-amino]-acetic acid a) 4-Hydroxy-7,8-dimethyl-2-oxo-2H-chromene-3-carboxylic acid ethyl ester A mixture of 2,3-dimethyl-phenol (1.17 g, 9.57 mmol), 2-ethoxycarbonyl-malonic acid diethyl ester (4.1 mL, 19.1 mmol), and tin tetrachloride (23 µL, 0.19 mmol) was heated in a 200° C.-oil bath for 10 min; then cooled, the reaction mixture was directly purified on silica gel column chromatography (eluent: ethyl acetate in dichloromethane: 20% to 80%) to give the desired title product (18 mg). ESI (m/z): 263 (M+H)$^+$.

b) [(4-Hydroxy-7,8-dimethyl-2-oxo-2H-chromene-3-carbonyl)-amino]-acetic acid

A mixture of 4-hydroxy-7,8-dimethyl-2-oxo-2H-chromene-3-carboxylic acid ethyl ester (18 mg, 0.069 mmol) and sodium glycinate (34 mg, 0.34 mmol) in methoxyethanol (5 mL) was refluxed for 16 h; then cooled, the solvent was removed, the residue was redissolved in water, acidified with 2 M HCl, the precipitates were collected and freeze dried to give the desired title product (16 mg). ESI (m/z): 292 (M+H)$^+$.

Example 11

{[4-Hydroxy-2-oxo-7-(4-phenoxy-phenyl)-2H-chromene-3-carbonyl]-amino}-acetic acid a) 2-Acetoxy-4-bromo-benzoic acid A mixture of 4-bromo-2-hydroxy-benzoic acid (12.35 g, 56.91 mmol), acetic anhydride (35.6 mL) and conc sulfuric acid (0.93 mL) was heated at 100° C. for 1 h; then cooled, poured into 400 g ice/water, stirred for several minutes, the white precipitates were collected with filtration, washed with water, then the white solids were oven vacuum dried at 50° C. for 3 days to give the desired product (11.62 g). $^1$H NMR (200 MHz, CDCl$_3$): δ (ppm)=7.95 (d, 1H, J=8.5 Hz), 7.48 (dd, 1H, J=2.0 Hz, 8.5 Hz), 7.32 (d, 1H, J=2.0 Hz).

b) 7-Bromo-4-hydroxy-2-oxo-2H-chromene-3-carboxylic acid methyl ester

A mixture of 2-acetoxy-4-bromo-benzoic acid (11.62 g, 44.85 mmol), 1-hydroxybenzotriazole (6.07 g, 44.85 mmol) and DCC (9.26 g, 44.85 mmol) in THF (100 mL) was stirred at rt for 1 h; then the mixture was cooled in a 4° C.-cold room overnight, the solids were filtered off and rinsed with 100 mL THF; then concentrated to give the intermediate HOBt active ester. This ester was dissolved in 100 mL THF, then treated with malonic acid dimethyl ester (5.93 g) and sodium hydride (2.34 g, 60% in mineral oil) in an ice/water bath for two hours; then the reaction mixture was poured into 400 mL ice/water, followed by extraction with ethyl acetate, washing with sat. NaCl solution and drying over sodium sulfate to give intermediate after concentration. This intermediate was refluxed in 150 methanol and 150 mL 10% hydrochloric acid for 2 h. Then cooled, poured into 1-L ice/water, solid was collected with filtration, washed with water and crystallized from dichloromethane/methanol to give the desired title product (3.415 g). ESI (m/z): 299 (M+H)$^+$.

c) 4-Hydroxy-2-oxo-7-(4-phenoxy-phenyl)-2H-chromene-3-carboxylic acid methyl ester A mixture of 7-bromo-4-hydroxy-2-oxo-2H-chromene-3-carboxylic acid methyl ester (256 mg, 0.855 mmol), 4-phenoxyphenylboric acid (211 mg, 0.984 mmol), Pd(PPh$_3$)$_4$ (99 mg, 0.086 mmol) and aqueous sodium carbonate solution (1.1 mL, 2 M) in 1,2-dimethoxyethane (5 mL) was refluxed for 2.5 h. Then cooled, the slurry was diluted with EtOAc and water, solids were filtered off over Celite; EtOAc phase was separated from aqueous, washed with sat. NaCl solution, dried over sodium sulfate, filtered, and concentrated; the crude material was crystallized from dichloromethane and methanol to give the desired product as white micro crystals (228 mg). $^1$H NMR (200 MHz, CDCl$_3$): δ (ppm)=14.58 (s, 1H), 8.04 (d, 1H, J=8.4 Hz), 7.61-7.04 (m, 11H), 4.04 (s, 3H).

d) {[4-Hydroxy-2-oxo-7-(4-phenoxy-phenyl)-2H-chromene-3-carbonyl]-amino}-acetic acid A mixture of 4-hydroxy-2-oxo-7-(4-phenoxy-phenyl)-2H-chromene-3-carboxylic acid methyl ester (75 mg, 0.193 mmol) and sodium glycinate (94 mg, 0.96 mmol) in methoxyethanol (10 mL) was refluxed for 18 h; then cooled, the solvent was removed, the residue was redissolved in water, acidified with 2 M HCl, the precipitates were collected and washed with water, air dried to give the desired title product (80 mg). ESI (m/z): 432 (M+H)$^+$.

Example 12

2-S-{[4-Hydroxy-2-oxo-7-(4-phenoxy-phenyl)-2H-chromene-3-carbonyl]-amino}-propionic acid A mixture of L-alanine (78 mg, 0.87 mmol) and NaOMe/MeOH (1.7 mL, 0.5 M) was concentrated, then 4-hydroxy-2-oxo-7-(4-phenoxy-phenyl)-2H-chromene-3-carboxylic acid methyl ester (68 mg, 0.17 mmol) and 2-methoxyethanol (10 mL) were added and the mixture was refluxed for 16 h; cooled, the solvent was removed, the residue was redissolved in water, acidified with 2 M HCl, the precipitates were collected and washed with water, air dried to give the desired title product (67 mg). ESI (m/z): 446 (M+H)$^+$.

Example 13

[(6,8-Dichloro-4-hydroxy-2-oxo-2H-chromene-3-carbonyl)-amino]-acetic acid a) 2-Acetoxy-3,5-dichloro-benzoic acid 2-Acetoxy-3,5-dichloro-benzoic acid was prepared from 2-hydroxy-3,5-dichloro-benzoic acid under condition analogous to example 2-a. $^1$H NMR (200 MHz, CDCl$_3$): δ (ppm)= 7.96 (d, J=2.7 Hz, 1H), 7.67 (d, J=2.3 Hz, 1H), 2.38 (s, 3H).

b) 6,8-Dichloro-4-hydroxy-2-oxo-2H-chromene-3-carboxylic acid methyl ester

To a mixture of 2-acetoxy-3,5-dichloro-benzoic acid (5.36 g, 21.5 mmol) in anhydrous THF (50 mL) at 0° C. was added HOBT (2.90 g, 21.5 mmol) and then DCC (4.44 g, 21.5 mmol). Resulting mixture was stirred at 0° C. for 1 h and the suspension was refrigerated overnight at −20° C. The precipitated solid (DCCU) was filtered off to give Solution 1. In another flask, dimethylmalonate (2.84 g, 21.5 mmol) was dissolved in anhydrous THF (50 mL) and cooled to 0° C., and to the mixture was added NaH solid (60% dispersed in mineral oil) (401 mg, 10.04 mmol). The suspension was stirred at 0° C. for 5 min prior to the addition of Solution 1. The resulting mixture was stirred at 0° C. for 5 min and at r.t. for 2.5 h and then concentrated in vacuo. The residue was diluted with water (150 mL) and extracted with diethyl ether (100 mL). Aqueous layer was filtered. The filtrate was acidified to pH=4 using 2 N HCl, and extracted with methylene chloride.

Organic layer was washed with brine, dried over MgSO$_4$, filtered, and concentrated. The residue was treated with (1/1) MeOH/10% HCl aqueous solution (40 mL) and refluxed for 2 h. After cooled, solid precipitate was collected by filtration to give a crude product. The product was triturated with hot MeOH (40 mL) and cooled. White solid was collected and dried to give the title compound (0.62 g). $^1$H NMR (200 MHz, CDCl$_3$): δ (ppm)=14.66 (s, 1H), 7.89 (d, J=2.4 Hz, 1H), 7.71 (d, J=2.4 Hz, 1H), 4.05 (s, 3H).

c) [(6,8-Dichloro-4-hydroxy-2-oxo-2H-chromene-3-carbonyl)-amino]-acetic acid

A mixture of 6,8-dichloro-4-hydroxy-2-oxo-2H-chromene-3-carboxylic acid methyl ester (400 mg, 1.39 mmol) and glycine sodium salt (674 mg, 6.94 mmol) in 2-methoxyethanol (14 mL) was heated to reflux overnight. Reaction mixture was concentrated and dissolved in water (100 mL). The solution was acidified by 1 N aq HCl to pH=2-3. White precipitate was collected, rinsed with water and methanol and dried to give the title compound (401 mg). MS ESI(−) m/e: 332, 330 (M−1).

Example 14

[(6,8-Dichloro-4-hydroxy-2-oxo-2H-chromene-3-carbonyl)-amino]-acetic acid ethyl ester a) [(6,8-Dichloro-4-hydroxy-2-oxo-2H-chromene-3-carbonyl)-amino]-acetic acid ethyl ester To a mixture of [(6,8-dichloro-4-hydroxy-2-oxo-2H-chromene-3-carbonyl)-amino]-acetic acid (100 mg, 0.30 mmol) in ethanol (6 mL) was added SOCl$_2$ dropwise. Resulting mixture was refluxed for 1.5 h. After cooled, white precipitate was collected, rinsed with ethanol and dried to give the title compound (94 mg). MS ESI(+) m/e: 362, 360 (M+1).

Example 15

[(4-Hydroxy-6,7-dimethyl-2-oxo-2H-chromene-3-carbonyl)-amino]-acetic acid a) [(4-Hydroxy-6,7-dimethyl-2-oxo-2H-chromene-3-carbonyl)-amino]-acetic acid ethyl ester 4-Hydroxy-6,7-dimethyl-chromen-2-one (500 mg, 2.4 mmol), triethylamine (368 uL, 2.64 mmol) and methylene chloride (4 mL) were placed together in a dry flask. Isocyanato-acetic acid ethyl ester (283 uL, 2.52 mmol) was added and the reaction was stirred overnight (24 h) at room temperature. The crude reaction mixture was purified using silica gel chromatography (SGC) (1% Methanol in Methylene Chloride) to provide the title compound in 85% yield. MS ESI(−) m/e: 318.33 (M−1).

b) [(4-Hydroxy-6,7-dimethyl-2-oxo-2H-chromene-3-carbonyl)-amino]-acetic acid

The above ester (200 mg, 0.626 mmol) was dissolved in a mixture of tetrahydrofuran (10 mL) and methanol (10 mL) 1N sodium hydroxide (1.88 mL) was added to the solution and the reaction was permitted to stir overnight (8 h) at ambient temperature. The reaction was concentrated in vacuo and the residue dissolved in water. The aqueous solution was treated with 1N hydrochloric acid (pH=3) to precipitate the product which was collected via filtration and dried to yield the title compound (175 mg, 96%.) MS ESI(−) m/e: 290.11 (M−1).

Example 16

[(6-Fluoro-4-hydroxy-2-oxo-2H-chromene-3-carbonyl)-amino]-acetic acid a) 6-Fluoro-4-hydroxy-chromen-2-one 1-(5-Fluoro-2-hydroxy-phenyl)-ethanone (1.54 g, 10 mmol) and diethylcarbonate (2.42 mL, 20 mmol) were placed in a dry flask and dissolved in anhydrous tetrahydrofuran (30 mL.) The solution was then added drop-wise via cannula to a rapidly stirring solution of potassium tert-butoxide in tetrahydrofuran (1.0 M, 30 mL) The reaction was permitted to stir overnight (10 h) at room temperature under positive pressure of nitrogen. The crude reaction was concentrated under reduced pressure and partitioned between methyl tert-butyl ether and water. The layers were separated and the organic phase discarded. The aqueous phase was acidified to pH 5 and extracted three times with equal volumes of methylene chloride. The combined organic phases were dried over sodium sulfate and concentrated to give the title compound (1.4 g, 78% yield.) MS ESI(−) m/e: 179.16 (M−1).

b) [(6-Fluoro-4-hydroxy-2-oxo-2H-chromene-3-carbonyl)-amino]-acetic acid ethyl ester The title compound was prepared under conditions analogous to Example 15(a). $^1$H NMR (200 MHz, CDCl$_3$): δ (ppm)=9.564 (1H, br s), 7.67 (1H, dd), 7.35 (2H, m), 4.316-4.161 (4H, m), 1.316 (3H, s).

c) [(6-Fluoro-4-hydroxy-2-oxo-2H-chromene-3-carbonyl)-amino]-acetic acid

The title compound was prepared under conditions analogous to Example 15(b). MS ESI(−) m/e: 280.19 (M−1).

Example 17

[(7-Fluoro-4-hydroxy-2-oxo-2H-chromene-3-carbonyl)-amino]-acetic acid a) 7-Fluoro-4-hydroxy-chromen-2-one The title compound was prepared under conditions analogous to Example 16(a) using 1-(4-fluoro-2-hydroxy-phenyl)-ethanone. MS ESI(−) m/e: 179.233 (M−1).

b) [(7-Fluoro-4-hydroxy-2-oxo-2H-chromene-3-carbonyl)-amino]-acetic acid ethyl ester The title compound was prepared under conditions analogous to Example 15(a). MS ESI(+) m/e: 310.2375 (M+1).

c) [(7-Fluoro-4-hydroxy-2-oxo-2H-chromene-3-carbonyl)-amino]-acetic acid

The title compound was prepared under conditions analogous to Example 15(b). MS ESI(−) m/e: 280.19 (M−1).

Example 18

[(6,8-Difluoro-4-hydroxy-2-oxo-2H-chromene-3-carbonyl)-amino]-acetic acid a) 6,8-Difluoro-4-hydroxy-chromen-2-one The title compound was prepared under conditions analogous to Example 16(a) using 1-(3,5-difluoro-2-hydroxy-phenyl)-ethanone. $^1$H NMR (200 MHz, d$_6$-DMSO): δ (ppm)=7.774-7.659 (1H, m), 7.399-7.333 (1H, m), 5.646 (1H, s).

b) [(6,8-Difluoro-4-hydroxy-2-oxo-2H-chromene-3-carbonyl)-amino]-acetic acid ethyl ester The title compound was prepared under conditions analogous to Example 15(a). MS ESI(−) m/e: 326.0928 (M−1).

c) [(6,8-Difluoro-4-hydroxy-2-oxo-2H-chromene-3-carbonyl)-amino]-acetic acid

The title compound was prepared under conditions analogous to Example 15(b). MS ESI(−) m/e: 298.20 (M−1).

Example 19

[(6-Chloro-4-hydroxy-8-methyl-2-oxo-2H-chromene-3-carbonyl)-amino]-acetic acid a) 8-Bromo-6-chloro-4-hydroxy-chromen-2-one The title compound was prepared under conditions analogous to Example 16(a) using 1-(3-bromo-5-chloro-2-hydroxy-phenyl)-ethanone. MS ESI(−) m/e: 275.158 (M−1).

b) [(8-Bromo-6-chloro-4-hydroxy-2-oxo-2H-chromene-3-carbonyl)-amino]-acetic acid ethyl ester The title compound was prepared under conditions analogous to Example 15(a). MS ESI(−) m/e: 403.8375 (M−1).

c) [(6-Chloro-4-hydroxy-8-methyl-2-oxo-2H-chromene-3-carbonyl)-amino]-acetic acid ethyl ester The above ester (290 mg, 0.717 mmol) was dissolved in anhydrous N,N-dimethylformamide (3 mL), tetramethyl tin (150 uL, 1.075 mmol), dichloro(bis-tripehnylphosphino) palladium (76 mg, 0.1075 mmol), and 4A molecular sieves were added sequentially to the reaction. The reaction was sealed and heated to 120 C in an oil bath for 20 min. The reaction was cooled, diluted with ethyl acetate, and partitioned with water. The organic phase was washed with water, brine, and dried over sodium sulfate. The crude material was purified by SGC (15%-60% Ethyl Acetate in Hexanes) to provide the title compound in 80% yield. MS ESI(+) m/e: 340.2184 (M+1).

d) [(6-Chloro-4-hydroxy-8-methyl-2-oxo-2H-chromene-3-carbonyl)-amino]-acetic acid The title compound was prepared under conditions analogous to Example 15(b). MS ESI(−) m/e: 310.24 (M−1).

Example 20

[(4-Hydroxy-8-methyl-2-oxo-2H-chromene-3-carbonyl)-amino]-acetic acid a) [(4-Hydroxy-8-methyl-2-oxo-2H-chromene-3-carbonyl)-amino]-acetic acid Compound 19(d) (125 mg, 0.40 mmol) was dissolved in 1N sodium hydroxide (1.2 mL) and water (8.8 mL). 10% palladium on carbon (15 mg) was added and the solution was vacuum-purged and treated with hydrogen gas (1 atm.) The reaction was permitted to stir overnight (16 h) at ambient temperature. The crude mixture was filtered through celite and the filter was washed with 1N sodium hydroxide. The aqueous phase was acidified to pH 3 with 1N hydrochloric acid and the product was collected by filtration to give the title compound (70 mg, 65% yield.) MS ESI(−) m/e: 276.25 (M−1).

Example 21

{[6-Chloro-4-hydroxy-8-(2-methyl-5-trifluoromethyl-2H-pyrazol-3-yl)-2-oxo-2H-chromene-3-carbonyl]-amino}-acetic acid a) {[6-Chloro-4-hydroxy-8-(2-methyl-5-trifluoromethyl-2H-pyrazol-3-yl)-2-oxo-2H-chromene-3-carbonyl]-amino}-acetic acid ethyl ester The title compound was prepared from compound 19(b) under conditions analogous to Example 19(c) using 1-methyl-5-tributylstannanyl-3-trifluoromethyl-1H-pyrazole. MS ESI(−) m/e: 472.24 (M−1).

b) {[6-Chloro-4-hydroxy-8-(2-methyl-5-trifluoromethyl-2H-pyrazol-3-yl)-2-oxo-2H-chromene-3-carbonyl]-amino}-acetic acid The title compound was prepared under conditions analogous to Example 15(b). MS ESI(−) m/e: 444.301 (M−1).

Example 22

{[4-Hydroxy-8-(2-methyl-5-trifluoromethyl-2H-pyrazol-3-yl)-2-oxo-2H-chromene-3-carbonyl]-amino}-acetic acid a) {[4-Hydroxy-8-(2-methyl-5-trifluoromethyl-2H-pyrazol-3-yl)-2-oxo-2H-chromene-3-carbonyl]-amino}-acetic acid The title compound was prepared under conditions analogous to Example 20(a) from compound 21(b). MS ESI(−) m/e: 410.0285 (M−1).

Example 23

[(6-Chloro-4-hydroxy-2-oxo-8-pyridin-3-yl-2H-chromene-3-carbonyl)-amino]-acetic acid a) [(6-Chloro-4-hydroxy-2-oxo-8-pyridin-3-yl-2H-chromene-3-carbonyl)-amino]-acetic acid ethyl ester The title compound was prepared from compound 19(b) under conditions analogous to Example 19(c) using 3-tributylstannanyl-pyridine. MS ESI(−) m/e: 401.268 (M−1).

b) [(6-Chloro-4-hydroxy-2-oxo-8-pyridin-3-yl-2H-chromene-3-carbonyl)-amino]-acetic acid The title compound was prepared under conditions analogous to Example 15(b). MS ESI(−) m/e: 373.258 (M−1).

Example 24

[(6-Chloro-4-hydroxy-2-oxo-8-phenyl-2H-chromene-3-carbonyl)-amino]-acetic acid a) [(6-Chloro-4-hydroxy-2-oxo-8-phenyl-2H-chromene-3-carbonyl)-amino]-acetic acid ethyl ester The title compound was prepared from compound 19(b) under conditions analogous to Example 19(c) using tributyl-phenyl-stannane. MS ESI(−) m/e: 400.248 (M−1).

b) [(6-Chloro-4-hydroxy-2-oxo-8-phenyl-2H-chromene-3-carbonyl)-amino]-acetic acid The title compound was prepared under conditions analogous to Example 15(b). MS ESI(+) m/e: 374.2102 (M+1).

Example 25

[(4-Hydroxy-2-oxo-8-phenyl-2H-chromene-3-carbonyl)-amino]-acetic acid a) [(4-Hydroxy-2-oxo-8-phenyl-2H-chromene-3-carbonyl)-amino]-acetic acid The title compound was prepared under conditions analogous to Example 20(a) using compound 24(b). MS ESI(−) m/e: 338.075 (M−1).

Example 26

[(6-Chloro-4-hydroxy-2-oxo-8-thiophen-2-yl-2H-chromene-3-carbonyl)-amino]-acetic acid a) [(6-Chloro-4-hydroxy-2-oxo-8-thiophen-2-yl-2H-chromene-3-carbonyl)-amino]-acetic acid ethyl ester The title compound was prepared from compound 19(b) under conditions analogous to Example 19(c) using tributyl-thiophen-2-yl-stannane. MS ESI(−) m/e: 406.230 (M−1).

b) [(6-Chloro-4-hydroxy-2-oxo-8-thiophen-2-yl-2H-chromene-3-carbonyl)-amino]-acetic acid The title compound was prepared under conditions analogous to Example 15(b). MS ESI(−) m/e: 378.1532 (M−1).

Example 27

[(4-Hydroxy-2-oxo-6-thiophen-2-yl-2H-chromene-3-carbonyl)-amino]-acetic acid a) [(6-Bromo-4-hydroxy-2-oxo-2H-chromene-3-carbonyl)-amino]-acetic acid ethyl ester The title compound was prepared under conditions analogous to Example 15(a) using 6-bromo-4-hydroxy-chromen-2-one. MS ESI(+) m/e: 371.9165 (M+1).

b) [(4-Hydroxy-2-oxo-6-thiophen-2-yl-2H-chromene-3-carbonyl)-amino]-acetic acid ethyl ester The title compound was prepared under conditions analogous to Example 19(c). MS ESI(−) m/e: 372.31 (M−1).

c) [(4-Hydroxy-2-oxo-6-thiophen-2-yl-2H-chromene-3-carbonyl)-amino]-acetic acid

The title compound was prepared under conditions analogous to Example 15(b). MS ESI(−) m/e: 344.16 (M−1).

Example 28

[(6-Furan-2-yl-4-hydroxy-2-oxo-2H-chromene-3-carbonyl)-amino]-acetic acid a) [(6-Bromo-4-hydroxy-2-oxo-2H-chromene-3-carbonyl)-amino]-acetic acid ethyl ester The title compound was prepared under conditions analogous to Example 15(a) using 6-bromo-4-hydroxy-chromen-2-one. MS ESI(+) m/e: 371.9165 (M+1).

b) [(6-Furan-2-yl-4-hydroxy-2-oxo-2H-chromene-3-carbonyl)-amino]-acetic acid ethyl ester The title compound was prepared under conditions analogous to Example 19(c). MS ESI(−) m/e: 356.0269 (M−1).

c) [(6-Furan-2-yl-4-hydroxy-2-oxo-2H-chromene-3-carbonyl)-amino]-acetic acid

The title compound was prepared under conditions analogous to Example 15(b). MS ESI(−) m/e: 328.25 (M−1).

Example 29

[(4-Hydroxy-2-oxo-6-pyridin-3-yl-2H-chromene-3-carbonyl)-amino]-acetic acid a) [(6-Bromo-4-hydroxy-2-oxo-2H-chromene-3-carbonyl)-amino]-acetic acid ethyl ester The title compound was prepared under conditions analogous to Example 15(a) using 6-bromo-4-hydroxy-chromen-2-one. MS ESI(+) m/e: 371.9165 (M+1).

b) [(4-Hydroxy-2-oxo-6-pyridin-3-yl-2H-chromene-3-carbonyl)-amino]-acetic acid ethyl ester The title compound was prepared under conditions analogous to Example 19(c). MS ESI(+) m/e: 369.3154 (M+1).

c) [(4-Hydroxy-2-oxo-6-pyridin-3-yl-2H-chromene-3-carbonyl)-amino]-acetic acid

The title compound was prepared under conditions analogous to Example 15(b). MS ESI(+) m/e: 341.2381 (M+1).

Example 30

[(4-Hydroxy-2-oxo-6-pyridin-2-yl-2H-chromene-3-carbonyl)-amino]-acetic acid a) [(6-Bromo-4-hydroxy-2-oxo-2H-chromene-3-carbonyl)-amino]-acetic acid ethyl ester The title compound was prepared under conditions analogous to Example 15(a) using 6-bromo-4-hydroxy-chromen-2-one. MS ESI(+) m/e: 371.9165 (M+1).

b) [(4-Hydroxy-2-oxo-6-pyridin-2-yl-2H-chromene-3-carbonyl)-amino]-acetic acid ethyl ester The title compound was prepared under conditions analogous to Example 19(c). MS ESI(+) m/e: 369.3154 (M+1).

c) [(4-Hydroxy-2-oxo-6-pyridin-2-yl-2H-chromene-3-carbonyl)-amino]-acetic acid

The title compound was prepared under conditions analogous to Example 15(b).

Example 31

[(4-Hydroxy-2-oxo-2H-benzo[h]chromene-3-carbonyl)-amino]-acetic acid a) 1-Acetoxy-naphthalene-2-carboxylic acid The title compound was prepared under conditions analogous to Example 2(a) using 1-acetoxy-naphthalene-2-carboxylic acid. The product was used directly without further purification.

b) 4-Hydroxy-2-oxo-2H-benzo[h]chromene-3-carboxylic acid methyl ester

The title compound was prepared under conditions analogous to Example 2(b). MS ESI(−) m/e: 269.24 (M−1).

c) [(4-Hydroxy-2-oxo-2H-benzo[h]chromene-3-carbonyl)-amino]-acetic acid

The title compound was prepared under conditions analogous to Example 9(b). MS ESI(−) m/e: 312.21 (M−1).

Example 32

[(4-Hydroxy-2-oxo-2H-benzo[g]chromene-3-carbonyl)-amino]-acetic acid a) 3-Acetoxy-naphthalene-2-carboxylic acid The title compound was prepared under conditions analogous to Example 2(a) using 3-hydroxy-naphthalene-2-carboxylic acid. The product was used directly without further purification.

b) 4-Hydroxy-2-oxo-2H-benzo[g]chromene-3-carboxylic acid methyl ester

The title compound was prepared under conditions analogous to Example 2(b). MS ESI(−) m/e: 269.18 (M−1).

c) [(4-Hydroxy-2-oxo-2H-benzo[g]chromene-3-carbonyl)-amino]-acetic acid

The title compound was prepared under conditions analogous to Example 9(b). MS ESI(−) m/e: 312.28 (M−1).

Example 33

[(1-Hydroxy-3-oxo-3H-benzo[f]chromene-2-carbonyl)-amino]-acetic acid a) 2-Acetoxy-naphthalene-1-carboxylic acid The title compound was prepared under conditions analogous to Example 2(a) using 2-hydroxy-naphthalene-1-carboxylic acid. The product was used directly without further purification.

b) 1-Hydroxy-3-oxo-3H-benzo[f]chromene-2-carboxylic acid methyl ester

The title compound was prepared under conditions analogous to Example 2(b). MS ESI(−) m/e: 269.24 (M−1).

c) [(1-Hydroxy-3-oxo-3H-benzo[f]chromene-2-carbonyl)-amino]-acetic acid

The title compound was prepared under conditions analogous to Example 9(b). MS ESI(−) m/e: 312.21 (M−1).

Example 34

[(7,10-Dibromo-4-hydroxy-2-oxo-2H-benzo[g]chromene-3-carbonyl)-amino]-acetic acid a) 3-Acetoxy-5,7-dibromo-naphthalene-2-carboxylic acid The title compound was prepared under conditions analogous to Example 2(a) using 4,7-dibromo-3-hydroxy-naphthalene-2-carboxylic acid. The product was used directly without further purification.

b) 7,10-Dibromo-4-hydroxy-2-oxo-2H-benzo[g]chromene-3-carboxylic acid methyl ester The title compound was prepared under conditions analogous to Example 2(b). MS ESI(+) m/e: 429.3450 (M+1).

c) [(7,10-Dibromo-4-hydroxy-2-oxo-2H-benzo[g]chromene-3-carbonyl)-amino]-acetic acid The title compound was prepared under conditions analogous to Example 9(b). MS ESI(−) m/e: 470.00 (M−1).

Example 35

[(4-Hydroxy-7-methyl-2-oxo-2H-chromene-3-carbonyl)-amino]-acetic acid a) [(7-Bromo-4-hydroxy-2-oxo-2H-chromene-3-carbonyl)-amino]-acetic acid A mixture of 7-bromo-4-hydroxy-2-oxo-2H-chromene-3-carboxylic acid methyl ester (example 11-b) (2.835 g, 9.47 mmol) and glycine sodium salt (13.8 g, 142.12 mmol) in 2-methoxyethanol (100 mL) was refluxed for 6 h; then cooled, solvent was evaporated, the residue was dissolved in water and acidified with 2 M HCl solution; the precipitates were collected via filtration, washed with water and air dried to give the desired title product (3.209 g). $^1$H NMR (200 MHz, DMSO-d6): δ (ppm)=18-12 (br, 2H), 9.79 (br, 1H), 7.85 (d, 1H, J=8.4 Hz), 7.7-7.5 (m, 2H), 4.05 (d, 2H, J=5.6 Hz).

b) [(7-Bromo-4-hydroxy-2-oxo-2H-chromene-3-carbonyl)-amino]-acetic acid ethyl ester A mixture of [(7-bromo-4-hydroxy-2-oxo-2H-chromene-3-carbonyl)-amino]-acetic acid (3.209 g, 9.38 mmol) and thionyl chloride (2.05 mL, 28.1 mmol) in ethanol (75 mL) was refluxed for 2 h; then cooled, the precipitates were collected via filtration and washed with cold ethanol, air dried to give the desired product (3.153 g). $^1$H NMR (200 MHz, CDCl$_3$): δ (ppm)=17.5 (s, 1H), 9.5 (br, 1H), 7.88 (dd, 1H, J=0.6 Hz, 8.4 Hz), 7.5-7.2 (m, 2H), 4.32-4.18 (m, 4H), 1.32 (t, 3H, J=7.0 Hz).

c) [(4-Hydroxy-7-methyl-2-oxo-2H-chromene-3-carbonyl)-amino]-acetic acid ethyl ester A mixture of [(7-bromo-4-hydroxy-2-oxo-2H-chromene-3-carbonyl)-amino]-acetic acid ethyl ester (212 mg, 0.563 mmol), tetramethyltin (0.158 mL, 1.14 mmol) and Pd(PPh$_3$)$_2$Cl$_2$ (20 mg, 0.029 mmol) in N,N-dimethylformamide (2 mL) was heated in a 120° C.-oil bath under nitrogen for 1 h; then cooled, diluted with ethyl acetate, washed with water, saturated NaCl solution, and ethyl acetate phase was dried over Na$_2$SO$_4$, filtered, concentrated and column purified to give desired product (106 mg). ESI (m/z): 306 (M+H)$^+$.

d) [(4-Hydroxy-7-methyl-2-oxo-2H-chromene-3-carbonyl)-amino]-acetic acid

A mixture of [(4-hydroxy-7-methyl-2-oxo-2H-chromene-3-carbonyl)-amino]-acetic acid ethyl ester (106 mg, 0.347 mmol) and NaOH solution (0.70 mL, 1.38 mmol) in tetrahydrofuran (3 mL), methanol (3 mL) and water (3 mL) was stirred at rt overnight; the solvents were evaporated and the resulting residue was dissolved in water, acidified with 2 M HCl solution, the precipitates were then dried to give the desired product (80 mg). ESI (m/z): 278 (M+H)$^+$.

Example 36

[(7-Chloro-4-hydroxy-2-oxo-2H-chromene-3-carbonyl)-amino]-acetic acid a) 7-Chloro-2,2-dimethyl-benzo[1,3]dioxin-4-one 10 mL of trifluoroacetic anhydride and 2 mL of acetone were added to a 0° C. slurry of 4-chlorosalicylic acid (2.23 g, 13 mmol) in 16 mL of trifluoroacetic acid. The mixture was allowed to slowly warm to room temperature and stirred for 25 hours under a nitrogen atmosphere. The tan solution was concentrated under vacuum, dissolved and re-concentrated from toluene twice, and dried under vacuum. The crude solid was dissolved in ethyl acetate and washed twice with saturated sodium bicarbonate solution and once with brine. The organic fraction was dried over sodium sulfate, and concentrated to a tan semi-solid, which was partially dissolved in 10 mL of dichloromethane and filtered to remove solids. The mother liquor was concentrated to give 1.28 g of a tan semi-solid. MS: (+) m/z 215.0/213.0 (M+1, $^{35/37}$Cl)

b) 7-Chloro-4-hydroxy-2-oxo-2H-chromene-3-carboxylic acid methyl ester

A solution of 750 mg 7-chloro-2,2-dimethyl-benzo[1,3]dioxin-4-one (3.53 mmol) and 1.42 mL dimethyl malonate (12.4 mmol) in 17 mL of anhydrous DMF was cooled to 0° C. with an external ice bath. To the cold solution was added 496 mg of sodium hydride (12.4 mmol, 60% dispersion in mineral oil), and the resultant mixture was stirred for ten minutes. The mixture was heated in a 115° C. sand bath for 18 hours. The resultant solution was cooled, and 13 mL of 1 N HCl and 30 mL water were added to precipitate a white solid. The solid was collected on a glass fritted filter and washed twice with water and once with methanol to give 784 mg of a white solid. MS: (+) m/z 255.02/257.00 (M+1, $^{35/37}$Cl)

c) [(7-Chloro-4-hydroxy-2-oxo-2H-chromene-3-carbonyl)-amino]-acetic acid

A suspension of 350 mg of 7-chloro-4-hydroxy-2-oxo-2H-chromene-3-carboxylic acid methyl ester (1.38 mmol) and 670 mg of sodium glycinate (6.9 mmol) in 13 mL of 2-methoxyethanol was heated at reflux temperature for 10 hours. The mixture was cooled acidified with 1N HCl and diluted with 10 mL water. The resultant white solid was collected on a glass fritted filter and washed twice with water and once with methanol. The solid was triturated with methanol to give 124 mg. MS: (+) m/z 298.03/300.02 (M+1, $^{35/37}$Cl)

Example 37

[(4-Hydroxy-6,8-diisopropyl-2-oxo-2H-chromene-3-carbonyl)-amino]-acetic acid a) 6,8-Diisopropyl-2,2-dimethyl-benzo[1,3]dioxin-4-one

The title compound was prepared from 3,5-diisopropyl-salicylic acid under conditions analogous to experimental example 36-a to give a crude product, which was further purified by column chromatography, eluting from silica gel with a gradient of 0 to 30% ethyl acetate in hexanes, to give the desired product as a clear oil. MS: (+) m/z 263.26 (M+1)

b) 4-Hydroxy-6,8-diisopropyl-2-oxo-2H-chromene-3-carboxylic acid methyl ester The title compound was prepared from 6,8-diisopropyl-2,2-dimethyl-benzo[1,3]dioxin-4-one under conditions analogous to experimental example 36-b to give a white solid product, which was further purified by column chromatography, eluting from silica gel with a gradient of 0 to 10% methanol in methylene chloride, to give the desired product as a white solid. MS: (+) m/z 305.11 (M+1)

c) [(4-Hydroxy-6,8-diisopropyl-2-oxo-2H-chromene-3-carbonyl)-amino]-acetic acid The title compound was prepared from 4-hydroxy-6,8-diisopropyl-2-oxo-2H-chromene-3-carboxylic acid methyl ester under conditions analogous to experimental example 36-c to give a white solid product, which was further purified by recrystallization from methanol. MS: (+) m/z 348.18 (M+1)

Example 38

[(6-Benzyloxy-4-hydroxy-2-oxo-2H-chromene-3-carbonyl)-amino]-acetic acid a) 6-Hydroxy-2,2-dimethyl-benzo[1,3]dioxin-4-one The title compound was prepared from 2,5-dihydroxybenzoic acid under conditions analogous to experimental example 36-a, with a reaction time of 48 hours, to give a crude solid product, which could be further purified by column chromatography, eluting from silica gel with a gradient of 5 to 50% ethyl acetate in hexanes, to give the desired product as a white solid. MS: (+) m/z 195.15 (M+1)

b) 6-Benzyloxy-2,2-dimethyl-benzo[1,3]dioxin-4-one

A mixture of 500 mg 6-hydroxy-2,2-dimethyl-benzo[1,3]dioxin-4-one (2.57 mmol), 550 mg benzyl bromide (3.22 mmol), and 922 mg cesium carbonate (2.8 mmol) in 8.6 mL of anhydrous DMF were stirred at room temperature for 18 hours. The mixture was diluted with ethyl acetate and washed successively with water, saturated sodium bicarbonate, and brine solutions. The organic fraction was dried over sodium sulfate and concentrated under reduced pressure to give a crude residue which was further purified by column chromatography, eluting from silica gel with a gradient of 10 to 50% ethyl acetate in hexanes, to give the desired product as a pale yellow solid. MS: (+) m/z 285.10 (M+1)

c) 6-Benzyloxy-4-hydroxy-2-oxo-2H-chromene-3-carboxylic acid methyl ester

The title compound was prepared from 6-Benzyloxy-2,2-dimethyl-benzo[1,3]dioxin-4-one under conditions analogous to experimental example 36-b, to give a crude solid product, which was further purified by recrystallization from ethyl acetate hexanes, to give the desired product as a white, needle-like, solid. MS: (+) m/z 327.08 (M+1)

d) [(6-Benzyloxy-4-hydroxy-2-oxo-2H-chromene-3-carbonyl)-amino]-acetic acid

The title compound was prepared from 6-benzyloxy-4-hydroxy-2-oxo-2H-chromene-3-carboxylic acid methyl ester under conditions analogous to experimental example 36-c, to give the desired product as a white solid. MS: (+) m/z 370.05 (M+1)

Example 39

[(6-Cyclohexylmethoxy-4-hydroxy-2-oxo-2H-chromene-3-carbonyl)-amino]-acetic acid a) 6-Cyclohexylmethoxy-2,2-dimethyl-benzo[1,3]dioxin-4-one The title compound was prepared from 6-hydroxy-2,2-dimethyl-benzo[1,3]dioxin-4-one (example 38.a) and (bromomethyl)cyclohexane under conditions analogous to experimental example 38-b, to give the desired product as a white solid. MS: (+) m/z 291.05 (M+1)

b) 6-Cyclohexylmethoxy-4-hydroxy-2-oxo-2H-chromene-3-carboxylic acid methyl ester The title compound was prepared from 6-cyclohexylmethoxy-2,2-dimethyl-benzo[1,3]dioxin-4-one under conditions analogous to experimental example 36-b, to give the desired product as a white solid. MS: (+) m/z 333.02 (M+1)

c) [(6-Cyclohexylmethoxy-4-hydroxy-2-oxo-2H-chromene-3-carbonyl)-amino]-acetic acid The title compound was prepared from 6-cyclohexylmethoxy-4-hydroxy-2-oxo-2H-chromene-3-carboxylic acid methyl ester under conditions analogous to experimental example 36-c, to give the desired product as a white solid. MS: (+) m/z 376.10 (M+1)

Example 40

[(6-Hexyloxy-4-hydroxy-2-oxo-2H-chromene-3-carbonyl)-amino]-acetic acid a) 6-Hexyloxy-2,2-dimethyl-benzo[1,3]dioxin-4-one The title compound was prepared from 6-hydroxy-2,2-dimethyl-benzo[1,3]dioxin-4-one (example 38-a) and (bromomethyl)cyclohexane under conditions analogous to experimental example 38-b, to give the desired product as a white solid. MS: (+) m/z 279.16 (M+1)

b) 6-Hexyloxy-4-hydroxy-2-oxo-2H-chromene-3-carboxylic acid methyl ester

The title compound was prepared from 6-hexyloxy-2,2-dimethyl-benzo[1,3]dioxin-4-one under conditions analogous to experimental example 36-b, to give the desired product as a white solid. MS: (+) m/z 321.04 (M+1)

c) [(6-Hexyloxy-4-hydroxy-2-oxo-2H-chromene-3-carbonyl)-amino]-acetic acid

The title compound was prepared from 6-hexyloxy-4-hydroxy-2-oxo-2H-chromene-3-carboxylic acid methyl ester under conditions analogous to experimental example 36-c, to give the desired product as a white solid. MS: (+) m/z 364.07 (M+1)

Example 41

(S)-2-[(7-Chloro-4-hydroxy-2-oxo-2H-chromene-3-carbonyl)-amino]-propionic acid

A mixture of 125 mg of 7-chloro-4-hydroxy-2-oxo-2H-chromene-3-carboxylic acid methyl ester (0.5 mmol), 534 mg of L-alanine (6 mmol), and 270 mg of sodium methoxide (5 mmol) in 8 mL of 2-methoxyethanol was heated at reflux for 18 hours. The mixture was cooled and acidified with 20 mL of 1 N HCl to precipitate a white solid. The solid was collected

Example 42

(S)-2-[(6-Hexyloxy-4-hydroxy-2-oxo-2H-chromene-3-carbonyl)-amino]-propionic acid The title compound was prepared from 6-hexyloxy-4-hydroxy-2-oxo-2H-chromene-3-carboxylic acid methyl ester, example 40-b, under conditions analogous to experimental example 41, with further purification of the crude product by recrystallization from methanol to give the desired product as a white solid. MS: (+) m/z 378.09 (M+1)

Example 43

(S)-2-[(6-Cyclohexylmethoxy-4-hydroxy-2-oxo-2H-chromene-3-carbonyl)-amino]-propionic acid The title compound was prepared from 6-cyclohexylmethoxy-4-hydroxy-2-oxo-2H-chromene-3-carboxylic acid methyl ester, example 39-c, under conditions analogous to experimental example 41, to give the desired product as a white solid. MS: (+) m/z 388.06 (M+1)

Example 44

[(4-Hydroxy-6-isopropoxy-2-oxo-2H-chromene-3-carbonyl)-amino]-acetic acid a) 6-Isopropoxy-2,2-dimethyl-benzo[1,3]dioxin-4-one The title compound was prepared from 6-hydroxy-2,2-dimethyl-benzo[1,3]dioxin-4-one (example 38-a) and 2-iodopropane under conditions analogous to experimental example 38-b, to give the desired product as a white solid. MS: (+) m/z 237.12 (M+1)

b) 4-Hydroxy-6-isopropoxy-2-oxo-2H-chromene-3-carboxylic acid methyl ester

The title compound was prepared from 6-isopropoxy-2,2-dimethyl-benzo[1,3]dioxin-4-one under conditions analogous to experimental example 36-b, to give the desired product as a white solid. MS: (+) m/z 279.10 (M+1)

c) [(4-Hydroxy-6-isopropoxy-2-oxo-2H-chromene-3-carbonyl)-amino]-acetic acid

The title compound was prepared from 4-hydroxy-6-isopropoxy-2-oxo-2H-chromene-3-carboxylic acid methyl ester under conditions analogous to experimental example 36-c, to give the desired product as a white solid. MS: (+) m/z 321.99 (M+1)

Example 45

[(8-Benzyloxy-4-hydroxy-2-oxo-2H-chromene-3-carbonyl)-amino]-acetic acid a) 8-Hydroxy-2,2-dimethyl-benzo[1,3]dioxin-4-one The title compound was prepared from 2,3-dihydroxybenzoic acid under conditions analogous to experimental example 36.a, with a reaction time of 72 hours, to give a crude solid product, which could be further purified by column chromatography, eluting from silica gel with a gradient of 5 to 60% ethyl acetate in hexanes, to give the desired product as a white solid. MS: (−) m/z 193.11 (M−1).

b) 8-Benzyloxy-2,2-dimethyl-benzo[1,3]dioxin-4-one

The title compound was prepared from 8-hydroxy-2,2-dimethyl-benzo[1,3]dioxin-4-one and benzylbromide under conditions analogous to experimental example 38-b, to give the desired product as an off-white solid. MS: (+) m/z 285.10 (M+1).

c) 8-Benzyloxy-4-hydroxy-2-oxo-2H-chromene-3-carboxylic acid methyl ester

The title compound was prepared from 8-benzyloxy-2,2-dimethyl-benzo[1,3]dioxin-4-one under conditions analogous to experimental example 36-b, to give the desired product as a white solid. MS: (+) m/z 327.03 (M+1).

d) [(8-Benzyloxy-4-hydroxy-2-oxo-2H-chromene-3-carbonyl)-amino]-acetic acid

The title compound was prepared from 8-benzyloxy-4-hydroxy-2-oxo-2H-chromene-3-carboxylic acid methyl ester under conditions analogous to experimental example 36-c, to give the desired product as a white solid. MS: (+) m/z 370.05 (M+1).

Example 46

[(5-Benzyloxy-4-hydroxy-2-oxo-2H-chromene-3-carbonyl)-amino]-acetic acid a) 5-Benzyloxy-2,2-dimethyl-benzo[1,3]dioxin-4-one To a mixture of 5-hydroxy-2,2-dimethyl-benzo[1,3]dioxin-4-one (Uchiyama M. et al *Org. Lett.* 2006, 8(24), 5517-5520) (2.0 g, 10.4 mmol) and benzyl bromide (1.78 g, 10.4 mmol) in DMF in an ice bath was added sodium hydride (60% dispersed in mineral oil, 624 mg, 15.6 mmol). Resulting mixture was stirred at 0° C. for 10 min and then at rt for 6 h. Reaction mixture was quenched with water (250 mL), neutralized using 1 N HCl to pH=6-7 and extracted with EtOAc (2×). Combined organic layers were washed with brine, dried over MgSO$_4$, filtered and concentrated. Crude product was triturated with hexanes (50 mL). Solid was collected and dried in vacuo to provide the title compound 2.5 g. $^1$H NMR (200 MHz, CDCl$_3$): δ (ppm)=7.54 (m, 2H), 7.37 (m, 4H), 6.57 (m, 2H), 5.25 (s, 2H), 1.71 (s, 6H).

b) 5-Benzyloxy-4-hydroxy-2-oxo-2H-chromene-3-carboxylic acid methyl ester

To a cold mixture of 5-benzyloxy-2,2-dimethyl-benzo[1,3]dioxin-4-one (220 mg, 0.78 mmol) and dimethyl malonate (258 mg, 1.95 mmol) in DMF (4 mL) in an ice bath was added sodium hydride (60% dispersed in mineral oil, 94 mg, 2.34 mmol). Resulting mixture was stirred at 0° C. for 5 min, and then heated in a 120° C. oil bath overnight. The reaction mixture was diluted with water (60 mL), acidified using 1 N HCl to pH=3-4 and extracted with EtOAc. Organic layer was washed with brine, dried over MgSO$_4$, filtered and concentrated. Residue was triturated with MeOH. Solid was collected and dried in vacuo to provide the title compound (45 mg). $^1$H NMR (200 MHz, CDCl$_3$): δ (ppm)=15.15 (s, 1H), 7.59-7.33 (m, 6H), 6.92 (d, J=8.2 Hz, 1H), 6.83 (d, J=8.8 Hz, 1H), 5.25 (s, 2H), 4.03 (s, 3H).

c) [(5-Benzyloxy-4-hydroxy-2-oxo-2H-chromene-3-carbonyl)-amino]-acetic acid

A mixture of 5-benzyloxy-4-hydroxy-2-oxo-2H-chromene-3-carboxylic acid methyl ester (54 mg, 0.17 mmol) and sodium glycinate (241 mg, 2.48 mmol) in 2-methoxyethanol was refluxed for 18 h and then concentrated. Residue was dissolved in water (60 mL) and acidified using 1 N HCl to pH=3-4. Precipitate was collected, rinsed with water and dried in vacuo. Crude product was triturated with hexanes. Solid was collected and dried to provide the title compound (45 mg). MS ESI(+) m/e: 370.13 (M+1).

Example 47

{[5-(4-Fluoro-benzyloxy)-4-hydroxy-2-oxo-2H-chromene-3-carbonyl]-amino}-acetic acid a) 5-(4-Fluoro-benzyloxy)-2,2-dimethyl-benzo[1,3]dioxin-4-one 5-(4-Fluoro-benzyloxy)-2,2-dimethyl-benzo[1,3]dioxin-4-one was prepared from 5-hydroxy-2,2-dimethyl-benzo[1,3]dioxin-4-one and 4-fluorobenzyl bromide under conditions analogous to example 46-a. Crude product was purified by silica gel chromatography (eluting with 40%-100% CH$_2$Cl$_2$ in hexanes) to provide the title compound. MS ESI(+) m/e: 303.06 (M+1).

b) 5-(4-Fluoro-benzyloxy)-4-hydroxy-2-oxo-2H-chromene-3-carboxylic acid methyl ester 5-(4-Fluoro-benzyloxy)-4-hydroxy-2-oxo-2H-chromene-3-carboxylic acid methyl ester was prepared from 5-(4-fluoro-benzyloxy)-2,2-dimethyl-benzo[1,3]dioxin-4-one under conditions analogous to example 46-b. $^1$H NMR (200 MHz, CDCl$_3$): δ (ppm)=15.20 (s, 1H), 7.51 (m, 3H), 7.09 (m, 2H), 6.90 (d, J=8.6 Hz, 1H), 6.79 (d, J=7.6 Hz, 1H), 5.20 (s, 2H), 4.02 (s, 3H).

c) {[5-(4-Fluoro-benzyloxy)-4-hydroxy-2-oxo-2H-chromene-3-carbonyl]-amino}-acetic acid {[5-(4-Fluoro-benzyloxy)-4-hydroxy-2-oxo-2H-chromene-3-carbonyl]-amino}-acetic acid was prepared from 5-(4-fluoro-benzyloxy)-4-hydroxy-2-oxo-2H-chromene-3-carboxylic acid methyl ester under conditions analogous to example 46-c. Crude product was triturated with MeOH. Solid was collected and dried to provide the title compound. MS ESI(−) m/e: 386.13 (M−1).

Example 48

{[4-Hydroxy-5-(4-methyl-benzyloxy)-2-oxo-2H-chromene-3-carbonyl]-amino}-acetic acid a) 2,2-Dimethyl-5-(4-methyl-benzyloxy)-benzo[1,3]dioxin-4-one 2,2-Dimethyl-5-(4-methyl-benzyloxy)-benzo[1,3]dioxin-4-one was prepared from 5-hydroxy-2,2-dimethyl-benzo[1,3]dioxin-4-one and 4-methylbenzyl bromide under conditions analogous to example 47-a. MS ESI(+) m/e: 299.12 (M+1).

b) 4-Hydroxy-5-(4-methyl-benzyloxy)-2-oxo-2H-chromene-3-carboxylic acid methyl ester 4-Hydroxy-5-(4-methyl-benzyloxy)-2-oxo-2H-chromene-3-carboxylic acid methyl ester was prepared from 2,2-Dimethyl-5-(4-methyl-benzyloxy)-benzo[1,3]dioxin-4-one under conditions analogous to example 46-b. $^1$H NMR (200 MHz, CDCl$_3$): δ (ppm)=15.07 (s, 1H), 7.53 (t, J=8.3 Hz, 1H), 7.37 (d, J=7.9 Hz, 2H), 7.19 (d, J=7.9 Hz, 2H), 6.89 (d, J=8.2 Hz, 1H), 6.82 (d, J=8.2 Hz, 1H), 5.20 (s, 2H), 4.01 (s, 3H), 2.37 (s, 3H).

c) {[4-Hydroxy-5-(4-methyl-benzyloxy)-2-oxo-2H-chromene-3-carbonyl]-amino}-acetic acid {[4-Hydroxy-5-(4-methyl-benzyloxy)-2-oxo-2H-chromene-3-carbonyl]-amino}-acetic acid was prepared from 4-hydroxy-5-(4-methyl-benzyloxy)-2-oxo-2H-chromene-3-carboxylic acid methyl ester under conditions analogous to example 46-c. MS ESI(−) m/e: 382.18 (M−1).

Example 49

2-(S)-{[5-(4-Fluoro-benzyloxy)-4-hydroxy-2-oxo-2H-chromene-3-carbonyl]-amino}-propionic acid To a mixture of 5-(4-fluoro-benzyloxy)-4-hydroxy-2-oxo-2H-chromene-3-carboxylic acid methyl ester (86 mg, 0.25 mmol) and L-alanine (334 mg, 3.75 mmol) in 2-methoxyethanol was added sodium methoxide (176 mg, 3.25 mmol). Resulting mixture was refluxed overnight and concentrated. Residue was dissolved in water (100 mL) and acidified using 1 N HCl to pH=3-4. Precipitate was collected, rinsed with water and dried. Crude product was triturated with MeOH. Solid was collected and dried in vacuo to provide the title compound (61 mg). MS ESI(+) m/e: 402.13 (M+1).

Example 50

2-(S)-{[4-Hydroxy-5-(4-methyl-benzyloxy)-2-oxo-2H-chromene-3-carbonyl]-amino}-propionic acid 2-(S)-{[4-Hydroxy-5-(4-methyl-benzyloxy)-2-oxo-2H-chromene-3-carbonyl]-amino}-propionic acid was prepared from 4-hydroxy-5-(4-methyl-benzyloxy)-2-oxo-2H-chromene-3-carboxylic acid methyl ester under conditions analogous to example 49-a. MS ESI(−) m/e: 396.14 (M−1).

Example 51

[(5-Cyclohexyloxy-4-hydroxy-2-oxo-2H-chromene-3-carbonyl)-amino]-acetic acid a) 5-Cyclohexyloxy-2,2-dimethyl-benzo[1,3]dioxin-4-one To a cold mixture of 5-hydroxy-2,2-dimethyl-benzo[1,3]dioxin-4-one (1 g, 5.21 mmol) and cyclohexanol (1.98 g, 19.8 mmol) and triphenyl phosphine (2.46 g, 9.38 mmol) in THF in an ice bath was added diisopropyl azodicarboxylate (DIAD) (1.94 g, 9.59 mmol). Resulting mixture was stirred at 0° C. for 15 min and then at rt for 1 h. Reaction mixture was concentrated and the residue was purified by silica gel chromatography (eluting with 50%-100% CH$_2$Cl$_2$ in hexanes) to provide the title compound (0.97 g). $^1$H NMR (200 MHz, CDCl$_3$): δ (ppm)=7.36 (t, J=8.2 Hz, 1H), 6.60 (d, J=8.6 Hz, 1H), 6.47 (d, J=8.2 Hz, 1H), 4.39 (m, 1H), 1.93-1.37 (m, 10H), 1.69 (s, 6H).

b) 5-Cyclohexyloxy-4-hydroxy-2-oxo-2H-chromene-3-carboxylic acid methyl ester

5-Cyclohexyloxy-4-hydroxy-2-oxo-2H-chromene-3-carboxylic acid methyl ester was prepared from 5-cyclohexyloxy-2,2-dimethyl-benzo[1,3]dioxin-4-one under conditions analogous to example 46-b. Crude product was then purified by silica gel chromatography (5%-60% EtOAc in CH$_2$Cl$_2$) to provide the title compound (0.25 g). $^1$H NMR (200 MHz, CDCl$_3$): δ (ppm)=14.75 (br s, 1H), 7.50 (t, J=8.3 Hz, 1H), 6.83 (d, J=8.2 Hz, 1H), 6.76 (d, J=8.5 Hz, 1H), 4.50 (m, 1H), 4.00 (s, 3H), 1.95-1.26 (m, 10H).

c) [(5-Cyclohexyloxy-4-hydroxy-2-oxo-2H-chromene-3-carbonyl)-amino]-acetic acid

[(5-Cyclohexyloxy-4-hydroxy-2-oxo-2H-chromene-3-carbonyl)-amino]-acetic acid was prepared from 5-Cyclohexyloxy-4-hydroxy-2-oxo-2H-chromene-3-carboxylic acid methyl ester under conditions analogous to example 47-c. MS ESI(−) m/e: 360.19 (M−1).

Example 52

2-(S)-[(5-Cyclohexyloxy-4-hydroxy-2-oxo-2H-chromene-3-carbonyl)-amino]-propionic acid 2-(S)-[(5-Cyclohexyloxy-4-hydroxy-2-oxo-2H-chromene-3-carbonyl)-amino]-propionic acid was prepared from 5-cyclohexyloxy-4-hydroxy-2-oxo-2H-chromene-3-carboxylic acid methyl ester under conditions analogous to example 49-a. MS ESI(−) m/e: 374.06 (M−1).

Example 53

[(7-Benzyloxy-4-hydroxy-2-oxo-2H-chromene-3-carbonyl)-amino]-acetic acid a) 7-Hydroxy-2,2-dimethyl-benzo[1,3]dioxin-4-one To a cold mixture of 2,4-dihydroxybenzoic acid (25.9 g, 168.1 mmol), acetone (12.7 g, 218.5 mmol) and DMAP (1.03 g, 8.4 mmol) in 1,2-dimethoxyethane (DME) (96 mL) in an ice bath was added thionyl chloride (26.0 g, 218.5 mml) slowly. Resulting mixture was stirred at 0° C. for 1 h and then at rt for 23 h. Reaction mixture was quenched at 0° C. with saturated NaHCO$_3$ solution (slowly with caution). After 200 mL of saturated NaHCO$_3$ solution was added, NaHCO$_3$ solid was added in small portion to the mixture until pH reaches 7-8. It was diluted with water (200 mL) and extracted with EtOAc (2×200 mL). Organic layers were combined and washed with brine, dried over MgSO$_4$, filtered and concentrated. Crude residue was triturated with CH$_2$Cl$_2$ (100 mL). Solid was collected and dried to provide the title compound (10.4 g). $^1$H NMR (200 MHz, DMSO-d6): δ (ppm)=7.66 (d, J=7.8 Hz, 1H), 6.59 (d, J=7.8 Hz, 1H), 6.36 (s, 1H), 1.65 (s, 6H).

b) 7-Benzyloxy-2,2-dimethyl-benzo[1,3]dioxin-4-one

7-Benzyloxy-2,2-dimethyl-benzo[1,3]dioxin-4-one was prepared from 7-hydroxy-2,2-dimethyl-benzo[1,3]dioxin-4-one and benzyl bromide under conditions analogous to example 47-a. $^1$H NMR (200 MHz, CDCl$_3$): δ (ppm)=7.85 (d, J=8.5 Hz, 1H), 7.39 (m, 5H), 6.71 (dd, J=8.7, 2.3 Hz, 1H), 6.48 (d, J=2.3 Hz, 1H), 5.09 (s, 2H), 1.72 (s, 6H).

c) 7-Benzyloxy-4-hydroxy-2-oxo-2H-chromene-3-carboxylic acid methyl ester

7-Benzyloxy-4-hydroxy-2-oxo-2H-chromene-3-carboxylic acid methyl ester was prepared from 7-benzyloxy-2,2-dimethyl-benzo[1,3]dioxin-4-one under conditions analogous to example 46-b. Crude product was recrystallized from hot EtOAc to provide the title compound. $^1$H NMR (200 MHz, CDCl$_3$): δ (ppm)=13.4 (s, 1H), 7.91 (d, J=9.1 Hz, 1H), 7.40 (m, 5H), 6.95 (dd, J=8.8, 2.0 Hz, 1H), 6.81 (d, J=2.0 Hz, 1H), 5.15 (s, 2H), 4.02 (s, 3H).

d) [(7-Benzyloxy-4-hydroxy-2-oxo-2H-chromene-3-carbonyl)-amino]-acetic acid

[(7-Benzyloxy-4-hydroxy-2-oxo-2H-chromene-3-carbonyl)-amino]-acetic acid was prepared from 7-benzyloxy-4-hydroxy-2-oxo-2H-chromene-3-carboxylic acid methyl ester under conditions analogous to example 46-c. MS ESI(−) m/e: 368.02 (M−1).

Example 54

2-(S)-[(7-Benzyloxy-4-hydroxy-2-oxo-2H-chromene-3-carbonyl)-amino]-propionic acid 2-(S)-[(7-Benzyloxy-4-hydroxy-2-oxo-2H-chromene-3-carbonyl)-amino]-propionic acid was prepared from 7-benzyloxy-4-hydroxy-2-oxo-2H-chromene-3-carboxylic acid methyl ester and L-alanine under conditions analogous to example 49-a. MS ESI(−) m/e: 382.03 (M−1).

Example 55

{[5-(3-Cyclopentyl-propoxy)-4-hydroxy-2-oxo-2H-chromene-3-carbonyl]-amino}-acetic acid a) 5-(3-Cyclopentyl-propoxy)-2,2-dimethyl-benzo[1,3]dioxin-4-one 5-(3-Cyclopentyl-propoxy)-2,2-dimethyl-benzo[1,3]dioxin-4-one was prepared from 5-hydroxy-2,2-dimethyl-benzo[1,3]dioxin-4-one and 3-Cyclopentyl-propan-1-ol under conditions analogous to example 51-a. $^1$H NMR (200 MHz, CDCl$_3$): δ (ppm)=7.39 (t, J=8.4 Hz, 1H), 6.57 (d, J=8.5 Hz, 1H), 6.50 (d, J=8.2 Hz, 1H), 4.05 (t, J=7.0 Hz, 2H), 1.94-1.47 (m, 11H), 1.69 (s, 6H), 1.12 (m, 2H).

b) 5-(3-Cyclopentyl-propoxy)-4-hydroxy-2-oxo-2H-chromene-3-carboxylic acid methyl ester 5-(3-Cyclopentyl-propoxy)-4-hydroxy-2-oxo-2H-chromene-3-carboxylic acid methyl ester was prepared from 5-(3-Cyclopentyl-propoxy)-2,2-dimethyl-benzo[1,3]dioxin-4-one under conditions analogous to example 46-b. $^1$H NMR (200 MHz, CDCl$_3$): δ (ppm)=14.98 (s, 1H), 7.53 (t, J=8.5 Hz, 1H), 6.86 (d, J=8.5 Hz, 1H), 6.73 (d, J=8.5 Hz, 1H), 4.10 (t, J=6.4 Hz, 2H), 4.02 (s, 3H), 1.94-0.85 (m, 13H).

c) {[5-(3-Cyclopentyl-propoxy)-4-hydroxy-2-oxo-2H-chromene-3-carbonyl]-amino}-acetic acid {[5-(3-Cyclopentyl-propoxy)-4-hydroxy-2-oxo-2H-chromene-3-carbonyl]-amino}-acetic acid was prepared from 5-(3-cyclopentyl-propoxy)-4-hydroxy-2-oxo-2H-chromene-3-carboxylic acid methyl ester under conditions analogous to example 46-c. Crude product was recrystallized from MeOH to provide the title compound. MS ESI(−) m/e: 388.09 (M−1).

Example 56

2-(S)-{[5-(3-Cyclopentyl-propoxy)-4-hydroxy-2-oxo-2H-chromene-3-carbonyl]-amino}-propionic acid A mixture of 5-(3-cyclopentyl-propoxy)-4-hydroxy-2-oxo-2H-chromene-3-carboxylic acid methyl ester (110 mg, 0.32 mmol) and L-alanine (424 mg, 4.76 mmol) in 2-methoxyethanol (9 mL) was added sodium methoxide (207 mg, 3.84 mmol). Resulting mixture was refluxed overnight and concentrated. Residue was dissolved in water (75 mL) and extracted with (1/1) EtOAc/hexanes which was discarded. The aqueous layer was acidified using 1 N HCl to pH=3-4 and extracted with EtOAc. Organic layer was washed with water, brine, dried over MgSO$_4$, filtered and concentrated to provide the title compound (99.4 mg). MS ESI(−) m/e: 402.10 (M−1).

Example 57

[(7-Cyclohexyloxy-4-hydroxy-2-oxo-2H-chromene-3-carbonyl)-amino]-acetic acid a) 7-Cyclohexyloxy-2,2-dimethyl-benzo[1,3]dioxin-4-one 7-Cyclohexyloxy-2,2-dimethyl-benzo[1,3]dioxin-4-one was prepared from 7-hydroxy-2,2-dimethyl-benzo[1,3]dioxin-4-one and cyclohexanol under conditions analogous to example 51-a. $^1$H NMR (200 MHz, CDCl$_3$): δ (ppm)=7.82 (d, J=8.8 Hz, 1H), 6.61 (dd, J=8.8, 2.4 Hz, 1H), 6.39 (d, J=2.0 Hz, 1H), 4.30 (m, 1H), 2.02-1.28 (m, 10H), 1.73 (s, 6H).

b) 7-Cyclohexyloxy-4-hydroxy-2-oxo-2H-chromene-3-carboxylic acid methyl ester

7-Cyclohexyloxy-4-hydroxy-2-oxo-2H-chromene-3-carboxylic acid methyl ester was prepared from 7-cyclohexyloxy-2,2-dimethyl-benzo[1,3]dioxin-4-one under conditions analogous to example 46-b. $^1$H NMR (200 MHz, CDCl$_3$): δ (ppm)=14.51 (s, 1H), 7.86 (d, J=8.8 Hz, 1H), 6.84 (dd, J=8.8, 2.4 Hz, 1H), 6.72 (d, J=2.4 Hz, 1H), 4.33 (m, 1H), 4.01 (s, 3H), 2.17-1.25 (m, 10H).

c) [(7-Cyclohexyloxy-4-hydroxy-2-oxo-2H-chromene-3-carbonyl)-amino]-acetic acid

To a mixture of 7-cyclohexyloxy-4-hydroxy-2-oxo-2H-chromene-3-carboxylic acid methyl ester (90 mg, 0.28 mmol) and sodium glycinate (275 mg, 2.83 mmol) in 2-methoxyethanol was microwaved at 150° C. for 1 h and then concentrated. Residue was dissolved in water (60 mL) and extracted with (1/1) EtOAc/hexanes which was discarded. The aqueous layer was acidified using 1 N HCl to pH=3-4 and extracted with EtOAc (2×). Combined organic layers were washed with brine, dried over MgSO$_4$, filtered and concentrated to provide the title compound (82 mg). MS ESI(−) m/e: 360.06 (M−1).

Example 58

2-(S)-[(7-Cyclohexyloxy-4-hydroxy-2-oxo-2H-chromene-3-carbonyl)-amino]-propionic acid A mixture of 7-cyclohexyloxy-4-hydroxy-2-oxo-2H-chromene-3-carboxylic acid methyl ester (80 mg, 0.25 mmol), L-alanine (224 mg, 2.5 mmol) and sodium methoxide (108 mg, 2 mmol) in 2-methoxyethanol (3.5 mL) was microwaved at 150° C. for 2 h and then concentrated. Residue was dissolved in water (70 mL) and extracted with (1/1) EtOAc/hexanes which was discarded. The aqueous layer was acidified using 1 N HCl to pH=3-4 and extracted with EtOAc (2×). Combined organic layers were washed with brine, dried over MgSO$_4$, filtered and concentrated to provide the title compound (68 mg). MS ESI(−) m/e: 374.07 (M−1).

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:
1. A compound of formula I:

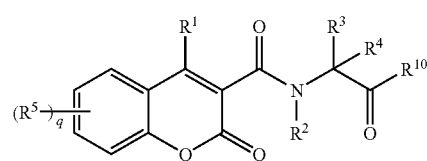

wherein:
q is 0, 1, 2, 3, or 4;
R$^1$ is hydroxyl;
R$^2$ is hydrogen;
R$^3$ is selected from the group consisting of hydrogen, deuterium, alkyl, and substituted alkyl;
R$^4$ is selected from the group consisting of hydrogen, deuterium, and methyl; and
each R$^5$ is independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl; or two R$^5$ taken together with the carbon atoms to which they are attached form an aryl, substituted aryl, cycloalkyl, substituted cycloalkyl, heterocyclic, substituted heterocyclic, heteroaryl or substituted heteroaryl;
R$^{10}$ is —NR$^{11}$R$^{12}$ or —OR$^{13}$;
R$^{11}$ and R$^{12}$ are independently selected from the group consisting hydrogen, alkyl, cycloalkyl-alkylene, (C$_3$-C$_8$)heterocyclic, aryl, —C(O)(C$_1$-C$_4$)alkyl, and alkyl-(C$_3$-C$_8$)cycloalkylene;

or $R^{11}$ and $R^{12}$ taken together with the nitrogen to which they are attached form a 5- or 6-membered heterocyclic or substituted heterocyclic; and $R^{13}$ is selected from the group consisting of hydrogen, a cation, and alkyl which is unsubstituted or substituted with one or more substituents independently selected from the group consisting of cycloalkyl, heterocyclic, aryl, and heteroaryl;

or a pharmaceutically acceptable salt, single stereoisomer, or mixture of stereoisomers thereof;

provided that the compound is not [(4-hydroxy-2-oxo-2H-chromene-3-carbonyl)-amino]-acetic acid.

2. A compound of formula II:

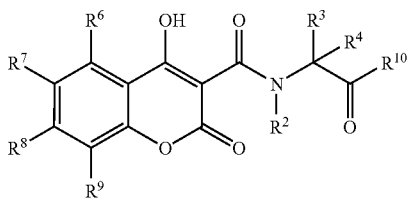

wherein $R^2$ is hydrogen;

$R^3$ is selected from the group consisting of hydrogen, deuterium, alkyl, and substituted alkyl;

$R^4$ is selected from the group consisting of hydrogen, deuterium, and methyl; and $R^6$ and $R^9$ are independently selected from the group consisting of hydrogen, halo, alkyl, alkoxy, substituted alkoxy, cycloalkyloxy, substituted cycloalkyloxy, aryl, substituted aryl, heteroaryl, and substituted heteroaryl;

$R^7$ and $R^8$ are independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl;

or one of $R^6$ and $R^7$, $R^7$ and $R^8$, or $R^8$ and $R^9$ taken together with the carbon atoms to which they are attached optionally form an aryl, substituted aryl, cycloalkyl, substituted cycloalkyl, heterocyclic, substituted heterocyclic, heteroaryl or substituted heteroaryl;

$R^{10}$ is —$NR^{11}R^{12}$ or —$OR^{13}$;

$R^{11}$ and $R^{12}$ are independently selected from the group consisting hydrogen, alkyl, cycloalkyl-alkylene, ($C_3$-$C_8$)heterocyclic, aryl, —C(O)($C_1$-$C_4$)alkyl, and alkyl-($C_3$-$C_8$)cycloalkylene;

or $R^{11}$ and $R^{12}$ taken together with the nitrogen to which they are attached form a 5- or 6-membered heterocyclic or substituted heterocyclic; and $R^{13}$ is selected from the group consisting of hydrogen, a cation, and alkyl which is unsubstituted or substituted with one or more substituents independently selected from the group consisting of cycloalkyl, heterocyclic, aryl, and heteroaryl;

or a pharmaceutically acceptable salt, single stereoisomer, or mixture of stereoisomers thereof;

provided that the compound is not [(4-hydroxy-2-oxo-2H-chromene-3-carbonyl)-amino]-acetic acid.

3. The compound of claim 1, wherein q is 1 or 2.

4. The compound of claim 1, wherein $R^4$ and $R^2$ are hydrogen.

5. The compound of claim 1, wherein each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl.

6. The compound of claim 1, wherein $R^{10}$ is —$OR^{13}$; and $R^{13}$ is selected from the group consisting of hydrogen, a cation, and alkyl which is unsubstituted or substituted with one or more substituents independently selected from the group consisting of cycloalkyl, heterocyclic, aryl, and heteroaryl.

7. The compound of claim 1, wherein $R^1$ is hydroxy;

$R^2$ and $R^4$ are hydrogen;

$R^3$ is selected from the group consisting of hydrogen, alkyl, and substituted alkyl; and each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl.

8. The compound of claim 1, wherein q is 1 or 2;

$R^1$ is hydroxy;

$R^2$ and $R^4$ are hydrogen;

$R^3$ is selected from the group consisting of hydrogen, alkyl, and substituted alkyl; and each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two $R^5$ taken together with the carbon atoms to which they are attached form an aryl or substituted aryl;

$R^{10}$ is —$OR^{13}$; wherein $R^{13}$ is hydrogen, a cation or alkyl.

9. The compound of claim 1, wherein q is 0;

$R^1$ is hydroxy;

$R^2$ and $R^4$ are hydrogen;

$R^3$ is selected from the group consisting of hydrogen, alkyl, and substituted alkyl; and $R^{10}$ is —$OR^{13}$; wherein $R^{13}$ is hydrogen, a cation or alkyl.

10. The compound of claim 1, wherein q is 1 or 2;

$R^1$ is hydroxy;

$R^2$ and $R^3$ are hydrogen;

$R^4$ is selected from the group consisting of hydrogen and methyl;

each $R^5$ is independently selected from the group consisting of hydrogen, halo, alkyl, substituted alkyl, aryl, substituted aryl, alkoxy, substituted alkoxy, cycloalkyloxy, aryloxy, substituted aryloxy, heteroaryl, and substituted heteroaryl; or two R⁵ taken together with the carbon atoms to which they are attached form an aryl or substituted aryl; and R¹⁰ is —OR¹³; wherein R¹³ is hydrogen, a cation or alkyl.

11. A compound selected from the group consisting of [(6-bromo-4-hydroxy-2-oxo-2H-chromene-3-carbonyl)-amino]-acetic acid; {[4-hydroxy-6-(4-methoxy-phenyl)-2-oxo-2H-chromene-3-carbonyl]-amino}-acetic acid; {[4-hydroxy-2-oxo-6-(4-phenoxy-phenyl)-2H-chromene-3-carbonyl]-amino}-acetic acid; {[4-hydroxy-2-oxo-6-(4-trifluoromethyl-phenyl)-2H-chromene-3-carbonyl]-amino}-acetic acid; [(4-hydroxy-6-methyl-2-oxo-2H-chromene-3-carbonyl)-amino]-acetic acid; [(8-Chloro-4-hydroxy-2-oxo-2H-chromene-3-carbonyl)-amino]-acetic acid; {[6-(4-benzyloxy-phenyl)-4-hydroxy-2-oxo-2H-chromene-3-carbonyl]-amino}-acetic acid; [(4-hydroxy-2-oxo-7-phenoxy-2H-chromene-3-carbonyl)-amino]-acetic acid; [(4-Hydroxy-7,8-dimethyl-2-oxo-2H-chromene-3-carbonyl)-amino]-acetic acid; {[4-hydroxy-2-oxo-7-(4-phenoxy-phenyl)-2H-chromene-3-carbonyl]-amino}-acetic acid; 2-(S)-{[4-hydroxy-2-oxo-7-(4-phenoxy-phenyl)-2H-chromene-3-carbonyl]-amino}-propionic acid; [(6,8-dichloro-4-hydroxy-2-oxo-2H-chromene-3-carbonyl)-amino]-acetic acid; [(6,8-dichloro-4-hydroxy-2-oxo-2H-chromene-3-carbonyl)-amino]-acetic acid ethyl ester; [(4-hydroxy-6,7-dimethyl-2-oxo-2H-chromene-3-carbonyl)-amino]-acetic acid; [(6-fluoro-4-hydroxy-2-oxo-2H-chromene-3-carbonyl)-amino]-acetic acid; [(7-fluoro-4-hydroxy-2-oxo-2H-chromene-3-carbonyl)-amino]-acetic acid; [(6,8-difluoro-4-hydroxy-2-oxo-2H-chromene-3-carbonyl)-amino]-acetic acid; [(6-chloro-4-hydroxy-8-methyl-2-oxo-2H-chromene-3-carbonyl)-amino]-acetic acid; [(4-hydroxy-8-methyl-2-oxo-2H-chromene-3-carbonyl)-amino]-acetic acid; {[6-chloro-4-hydroxy-8-(2-methyl-5-trifluoromethyl-2H-pyrazol-3-yl)-2-oxo-2H-chromene-3-carbonyl]-amino}-acetic acid; {[4-hydroxy-8-(2-methyl-5-trifluoromethyl-2H-pyrazol-3-yl)-2-oxo-2H-chromene-3-carbonyl]-amino}-acetic acid; [(6-chloro-4-hydroxy-2-oxo-8-pyridin-3-yl-2H-chromene-3-carbonyl)-amino]-acetic acid; [(6-chloro-4-hydroxy-2-oxo-8-phenyl-2H-chromene-3-carbonyl)-amino]-acetic acid; [(4-hydroxy-2-oxo-8-phenyl-2H-chromene-3-carbonyl)-amino]-acetic acid; [(6-chloro-4-hydroxy-2-oxo-8-thiophen-2-yl-2H-chromene-3-carbonyl)-amino]-acetic acid; [(4-hydroxy-2-oxo-6-thiophen-2-yl-2H-chromene-3-carbonyl)-amino]-acetic acid; [(6-furan-2-yl-4-hydroxy-2-oxo-2H-chromene-3-carbonyl)-amino]-acetic acid; [(4-hydroxy-2-oxo-6-pyridin-3-yl-2H-chromene-3-carbonyl)-amino]-acetic acid; [(4-hydroxy-2-oxo-6-pyridin-2-yl-2H-chromene-3-carbonyl)-amino]-acetic acid; [(4-hydroxy-2-oxo-2H-benzo[h]chromene-3-carbonyl)-amino]-acetic acid; [(4-hydroxy-2-oxo-2H-benzo[g]chromene-3-carbonyl)-amino]-acetic acid; [(1-hydroxy-3-oxo-3H-benzo[f]chromene-2-carbonyl)-amino]acetic acid; [(7,10-Dibromo-4-hydroxy-2-oxo-2H-benzo[g]chromene-3-carbonyl)-amino]acetic acid; [(4-hydroxy-7-methyl-2-oxo-2H-chromene-3-carbonyl)-amino]-acetic acid; [(7-chloro-4-hydroxy-2-oxo-2H-chromene-3-carbonyl)-amino]-acetic acid; [(4-hydroxy-6,8-diisopropyl-2-oxo-2H-chromene-3-carbonyl)-amino]-acetic acid; [(6-benzyloxy-4-hydroxy-2-oxo-2H-chromene-3-carbonyl)-amino]-acetic acid; [(6-cyclohexylmethoxy-4-hydroxy-2-oxo-2H-chromene-3-carbonyl)-amino]-acetic acid; [(6-hexyloxy-4-hydroxy-2-oxo-2H-chromene-3-carbonyl)-amino]-acetic acid; (S)-2-[(7-chloro-4-hydroxy-2-oxo-2H-chromene-3-carbonyl)-amino]-propionic acid; (S)-2-[(6-hexyloxy-4-hydroxy-2-oxo-2H-chromene-3-carbonyl)-amino]-propionic acid; (S)-2-[(6-cyclohexylmethoxy-4-hydroxy-2-oxo-2H-chromene-3-carbonyl)-amino]-propionic acid; [(4-hydroxy-6-isopropoxy-2-oxo-2H-chromene-3-carbonyl)-amino]-acetic acid; [(8-benzyloxy-4-hydroxy-2-oxo-2H-chromene-3-carbonyl)-amino]-acetic acid; [(5-benzyloxy-4-hydroxy-2-oxo-2H-chromene-3-carbonyl)-amino]-acetic acid; {[5-(4-fluoro-benzyloxy)-4-hydroxy-2-oxo-2H-chromene-3-carbonyl]-amino}-acetic acid; {[4-hydroxy-5-(4-methyl-benzyloxy)-2-oxo-2H-chromene-3-carbonyl]-amino}-acetic acid; 2-(S)-{[5-(4-fluoro-benzyloxy)-4-hydroxy-2-oxo-2H-chromene-3-carbonyl]-amino}-propionic acid; 2-(S)-{[4-hydroxy-5-(4-methyl-benzyloxy)-2-oxo-2H-chromene-3-carbonyl]-amino}-propionic acid; [(5-cyclohexyloxy-4-hydroxy-2-oxo-2H-chromene-3-carbonyl)-amino]-acetic acid; 2-(S)-[(5-cyclohexyloxy-4-hydroxy-2-oxo-2H-chromene-3-carbonyl)-amino]-propionic acid; [(7-benzyloxy-4-hydroxy-2-oxo-2H-chromene-3-carbonyl)-amino]-acetic acid; 2-(S)-[(7-benzyloxy-4-hydroxy-2-oxo-2H-chromene-3-carbonyl)-amino]-propionic acid; {[5-(3-cyclopentyl-propoxy)-4-hydroxy-2-oxo-2H-chromene-3-carbonyl]-amino}-acetic acid; 2-(S)-{[5-(3-cyclopentyl-propoxy)-4-hydroxy-2-oxo-2H-chromene-3-carbonyl]-amino}-propionic acid; [(7-cyclohexyloxy-4-hydroxy-2-oxo-2H-chromene-3-carbonyl)-amino]-acetic acid; and 2-(S)-[(7-cyclohexyloxy-4-hydroxy-2-oxo-2H-chromene-3-carbonyl)-amino]-propionic acid or a pharmaceutically acceptable salt, single stereoisomer, or mixture of stereoisomers thereof.

12. A pharmaceutical composition comprising one or more compounds of claim 1 and a pharmaceutically acceptable excipient.

13. The composition of claim 12, further comprising at least one additional therapeutic agent selected from the group consisting of vitamin $B_{12}$, folic acid, ferrous sulfate, recombinant human erythropoietin, and an erythropoiesis stimulating agent (ESA).

14. A method of inhibiting the activity of a HIF hydroxylase enzyme in vitro, the method comprising bringing into contact the HIF hydroxylase enzyme and an inhibitory-effective amount of a compound of formula I:

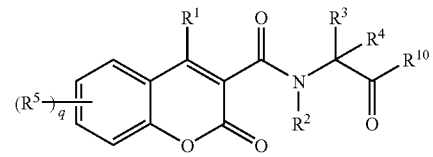

wherein:
q is 0, 1, 2, 3, or 4;
R¹ is hydroxy;
R² is hydrogen;
R³ is selected from the group consisting of hydrogen, deuterium, alkyl, and substituted alkyl;
R⁴ is selected from the group consisting of hydrogen, deuterium, and methyl; and
each R⁵ is independently selected from the group consisting of hydrogen, hydroxy, cyano, halo, nitro, acyl, amino, substituted amino, acylamino, sulfonyl, substituted sulfonyl, alkyl, substituted alkyl, alkenyl, substituted alkenyl, alkynyl, substituted alkynyl, alkoxy, substituted alkoxy, cycloalkyloxy, substituted cycloalkyloxy, heterocyclyloxy, substituted heterocyclyloxy, aryl, substituted aryl, aryloxy, substituted aryloxy, heteroaryloxy, substituted heteroaryloxy, alkylthio, substituted alkylthio, cycloalkylthio, substituted cycloalkylthio, arylthio, substituted arylthio, heteroarylthio, substituted heteroarylthio, heterocyclicthio, substituted heterocyclicthio, heteroaryl, and substituted heteroaryl; or two $R^5$ taken together with the carbon atoms to which they are attached form an aryl, substituted aryl, heteroaryl or substituted heteroaryl;

$R^{10}$ is $-NR^{11}R^{12}$ or $-OR^{13}$;

$R^{11}$ and $R^{12}$ are independently selected from the group consisting hydrogen, alkyl, cycloalkyl-alkylene, ($C_3$-$C_8$)heterocyclic, aryl, $-C(O)(C_1$-$C_4)$alkyl, and alkyl-($C_3$-$C_8$)cycloalkylene;

or $R^{11}$ and $R^{12}$ taken together with the nitrogen to which they are attached form a 5- or 6-membered heterocyclic or substituted heterocyclic; and $R^{13}$ is selected from the group consisting of hydrogen, a cation, and alkyl which is unsubstituted or substituted with one or more substituents independently selected from the group consisting of cycloalkyl, heterocyclic, aryl, and heteroaryl;

or a pharmaceutically acceptable salt, single stereoisomer, or mixture of stereoisomers thereof.

15. The method of claim 14, wherein the HIF hydroxylase enzyme is an asparaginyl hydroxylase.

16. The method of claim 15, wherein the asparaginyl hydroxylase is Factor inhibiting HIF (FIH).

17. The method of claim 14, wherein the HIF hydroxylase enzyme is a prolyl hydroxylase.

18. The method of claim 17, wherein the prolyl hydroxylase is selected from the group consisting of human EGLN1, EGLN2, and EGLN3.

\* \* \* \* \*